United States Patent
Elsen et al.

(10) Patent No.: US 10,363,208 B2
(45) Date of Patent: *Jul. 30, 2019

(54) METHODS FOR IMPROVING THE DURABILITY OF COLOR IN ARTIFICIALLY COLORED HAIR

(71) Applicant: L'OREAL, Paris (FR)

(72) Inventors: Andrea Elsen, Linden, NJ (US); Nghi Van Nguyen, Edison, NJ (US); Jim Singer, South Orange, NJ (US); Daniella Gonzalez-Toro, Hoboken, NJ (US); Martin Asare, Springfield, NJ (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/691,043

(22) Filed: Aug. 30, 2017

(65) Prior Publication Data

US 2019/0060196 A1    Feb. 28, 2019

(51) Int. Cl.
| | | |
|---|---|---|
| *A61Q 5/10* | (2006.01) | |
| *A61K 8/365* | (2006.01) | |
| *A61K 8/20* | (2006.01) | |
| *A61K 8/22* | (2006.01) | |
| *A61K 8/58* | (2006.01) | |

(52) U.S. Cl.
CPC ............ *A61K 8/365* (2013.01); *A61K 8/20* (2013.01); *A61K 8/22* (2013.01); *A61K 8/585* (2013.01); *A61Q 5/10* (2013.01); *A61K 2800/884* (2013.01)

(58) Field of Classification Search
CPC ... A61Q 5/10; A61K 8/20; A61K 8/22; A61K 8/365; A61K 8/46; A61K 2800/43; A61K 2800/882
See application file for complete search history.

(56) References Cited

U.S. PATENT DOCUMENTS

| | | | |
|---|---|---|---|
| 5,006,127 A | 4/1991 | Lorenz | |
| 5,346,509 A | 9/1994 | Prota | |
| 5,368,610 A | 11/1994 | Wenke | |
| 5,525,123 A | 6/1996 | Lorenz | |
| 5,708,151 A | 1/1998 | Mockli | |
| 6,616,707 B2 | 9/2003 | Lorenz | |
| 7,713,310 B2 | 5/2010 | Lalleman | |
| 8,337,570 B2 | 12/2012 | Schafer | |
| 8,883,127 B2 | 11/2014 | Pratt | |
| 9,375,393 B2 | 6/2016 | Lalleman | |
| 2002/0189031 A1* | 12/2002 | Javet | A61K 8/19 8/405 |
| 2005/0142090 A1 | 6/2005 | Watanabe | |
| 2007/0251024 A1 | 11/2007 | Greaves et al. | |
| 2008/0134449 A1 | 6/2008 | Lalleman | |
| 2008/0229521 A1 | 9/2008 | Lalleman | |
| 2008/0260672 A1 | 10/2008 | Oshimura | |
| 2013/0340783 A1 | 12/2013 | Lallenman | |
| 2013/0340784 A1 | 12/2013 | Lalleman | |
| 2015/0265525 A1 | 9/2015 | Benn | |
| 2017/0165160 A1 | 6/2017 | Krohn | |

FOREIGN PATENT DOCUMENTS

| | | |
|---|---|---|
| DE | 19904291 A1 | 8/2000 |
| EP | 0714954 A2 | 6/1996 |
| EP | 1915981 A1 | 4/2008 |
| EP | 1923042 A2 | 5/2008 |
| EP | 2246039 A1 | 11/2010 |
| WO | 95/01772 A2 | 1/1995 |
| WO | 95/15144 A2 | 6/1995 |
| WO | 2011/045404 A2 | 4/2011 |
| WO | 2012/084867 A2 | 6/2012 |
| WO | WO-2012/084473 A1 | 6/2012 |

OTHER PUBLICATIONS

U.S. Appl. No. 15/691,004, filed Aug. 30, 2017.
International Search Report and Written Opinion dated Dec. 19, 2018 for corresponding PCT Application No. PCT/US2018/048484.

* cited by examiner

*Primary Examiner* — Eisa B Elhilo
(74) *Attorney, Agent, or Firm* — Polsinelli PC

(57) ABSTRACT

The present disclosure relates to compositions and methods for improving the quality and durability of color in artificially colored hair. The methods employ pre-color treatments containing divalent metal salts of inorganic acids and monovalent or divalent metal salts of organic acids (treatments to the hair prior to artificial coloring of hair) and optionally, post-color treatments containing silane compounds (treatments to the hair after artificial coloring of hair).

37 Claims, No Drawings

METHODS FOR IMPROVING THE DURABILITY OF COLOR IN ARTIFICIALLY COLORED HAIR

FIELD OF THE DISCLOSURE

The present disclosure relates to methods and compositions for providing color protection to hair, in particular, for improving artificial color deposit and the durability of color in artificially colored hair.

BACKGROUND

There are many products available for changing the natural color of hair. The process of changing the color of hair can involve either depositing an artificial color onto the hair, which provides a different shade or color to the hair, or lifting the color of the hair, such as for example, from a dark brown shade to a medium brown or a light brown shade. Hair color can be changed using permanent, semi-permanent, or temporary hair coloring products.

Many consumers desire a permanent color change and therefore use products containing permanent dyes. Conventional permanent hair coloring products are dye compositions comprising oxidation dye precursors, which are also known as primary intermediates or couplers. These oxidation dye precursors are colorless or weakly colored compounds which, when combined with oxidizing products, give rise to colored complexes by a process of oxidative condensation. The oxidizing products conventionally use peroxides such as hydrogen peroxide as oxidizing agents. Such permanent hair color products also contain ammonia or other alkalizing agents such as monoethanolamine (MEA) which causes the hair shaft to swell, thus allowing the small oxidative dye molecules to penetrate the cuticle and cortex before the oxidation condensation process is completed. The resulting larger-sized colored complexes from the oxidative reaction are then trapped inside the hair fiber, thereby permanently altering the color of the hair.

Newly, permanently colored hair usually has a vibrant, shiny, and rich appearance. Unfortunately, however, in just a few short weeks, or in some cases even less, the color begins to fade due to washing, including shampooing, or exposure to environmental conditions. For instance, gorgeous rich brown colors become muddy and dull, beautiful shades of blonde turn brassy, and vibrant reds do not look so vibrant anymore acquiring golden, orange or brownish tonalities not desirable to the consumer. As described herein, the inventors of the instant disclosure have developed composition, methods and kits that improve color deposit onto hair and/or color durability by preventing color fading from hair. As described herein, the inventors of the instant disclosure have developed methods, compositions, and kits that improve color deposition and color durability by preventing color fading from hair.

SUMMARY OF THE DISCLOSURE

The present disclosure relates to improving color deposit on hair and the durability of the color in artificially colored hair. The methods described herein employ a combination of alkaline earth and alkali metal salts for use on hair before the hair is artificially colored or dyed. When these metal salts are used in the compositions and methods described herein, color deposit, color quality, and color durability are improved In one aspect, the invention of the present disclosure is directed to a method for artificially coloring hair and inhibiting the coloring from fading, the method comprising:

(a) treating hair with a pre-color treatment composition comprising about 0.5 wt. % to about 50 wt. % of one or more divalent metal salts of an inorganic acid and about 0.5 wt. % to about 50 wt. % of one or more monovalent or divalent metal salts of an organic acid; and (b) treating the hair with a hair coloring composition comprising one or more colorants chosen from oxidative dye precursors, direct dyes, pigments, and mixtures thereof.

all weights being based on the total weight of the pre-color treatment composition.

The above-described hair coloring composition further comprises one or more oxidizing agents or is capable of being mixed with an oxidizing composition comprising: (i) one or more oxidizing agents; and (ii) a cosmetically acceptable solvent chosen from water and a water/organic solvent mixture; wherein the one or more oxidizing agents are chosen from peroxides, persulfates, perborates, percarbonates, alkali metal bromates, ferricyanides, laccases, peroxidases, redox enzymes, their salts thereof, and mixtures thereof.

In another aspect, the method of the present disclosure further comprises a step of applying a post-color treatment composition onto the hair that has been treated with the hair coloring composition, wherein the post-color treatment composition contains from about 1 wt. % to about 30 wt. %, based on the total weight of the composition, of one or more silane compounds corresponding to formula (Ia):

$$R_1Si(OR_2)_z(R_3)_x(OH)_y \tag{Ia}$$

in which:

R1 is a cyclic or acyclic, linear or branched, saturated or unsaturated C1-C22, in particular C2-C20, hydrocarbon-based chain, which may be substituted with a group chosen from amine groups NH2 or NHR (R being a linear or branched C1-C20, in particular C1-C6, alkyl, a C3-C40 cycloalkyl or a C6-C30 aromatic radical); the hydroxyl group (OH), a thiol group, an aryl group (more particularly benzyl), which is possibly substituted with an NH2 or NHR group; it being possible for R1 to be interrupted with a heteroatom (O, S or NH) or a carbonyl group (CO), R2 and R3, which may be identical or different, represent a linear or branched alkyl group comprising from 1 to 6 carbon atoms, y denotes an integer ranging from 0 to 3, and z denotes an integer ranging from 0 to 3, and x denotes an integer ranging from 0 to 2, with z+x+y=3.

Finally, the instant disclosure relates to kits comprising the various compositions used to carry out the methods described herein. The kits may be used by hair-care professionals and salons for treating the hair of patrons or the kits may be purchased and used at home directly by consumers.

It is to be understood that both the foregoing general description and the following detailed description are exemplary and explanatory only, and are not restrictive of the disclosure.

Other subjects, characteristics, aspects and advantages of embodiments of the disclosure will emerge even more clearly on reading the description and the various examples that follow.

DETAILED DESCRIPTION OF THE DISCLOSURE

As used herein, the expression "one or more" means at least one and thus includes individual components as well as mixtures/combinations.

The terms "a," "an," and "the" are understood to encompass the plural as well as the singular.

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9%-11% and "about 2%" means 1.8%-2.2%), such as within 9%, 8%, 7%, 6%, 5%, 4%, 3%, 2%, or 1%, according to various embodiments.

The term "comprising" (and its grammatical variations) as used herein is used in the inclusive sense of "having" or "including" or "containing" and not in the exclusive sense of "consisting only of".

As used herein, the terms "applying a composition onto hair" and all its grammatical variations, include "contacting hair with a composition" or "exposing hair to a composition" or "layering a composition onto hair" or "treating hair with a composition" with any suitable means, for example, by using the hands or fingers, or an applicator such as a brush or comb, or by spraying, or by delivering through a nozzle or bottle cap tip.

As used herein, "formed from," means obtained from chemical reaction of, wherein "chemical reaction," includes spontaneous chemical reactions and induced chemical reactions. As used herein, the phrase "formed from," is open ended and does not limit the components of the composition to those listed.

The terms "organic acid" mean compounds containing carbon atoms and hydrogen atoms and optionally heteroatoms such as S, O, N or P, alone or in combination.

When referring to "compositions described herein," all types of compositions are intended unless specifically described otherwise. The "compositions disclosed herein" include the compositions comprising one or more reducing agent, the composition comprising one or more lactones, to oxidizing compositions, etc.

The compositions and methods of the present disclosure can comprise, consist of, or consist essentially of the essential elements and limitations of the disclosure described herein, as well as any additional or optional ingredients, components, or limitations described herein or otherwise useful.

An embodiment of the present disclosure is directed to a method for artificially coloring hair and inhibiting the coloring from fading, the method comprising:

(a) treating hair with a pre-color treatment composition comprising about 0.5 wt. % to about 50 wt. % of one or more divalent metal salts of an inorganic acid and about 0.5 wt. % to about 50 wt. % of one or more monovalent or divalent metal salts of an organic acid; and (b) treating the hair with a hair coloring composition comprising one or more colorants chosen from oxidative dye precursors, direct dyes, pigments, and mixtures thereof.

all weights being based on the total weight of the pre-color treatment composition.

In another aspect, the method of the present disclosure further comprises a step of applying a post-color treatment composition onto the hair that has been treated with the hair coloring composition, wherein the post-color treatment composition contains from about 1 wt. % to about 30 wt. %, based on the total weight of the composition, of one or more silane compounds corresponding to formula (Ia):

$$R1Si(OR2)z(R3)x(OH)y \quad \text{(Ia)}$$

in which:

R1 is a cyclic or acyclic, linear or branched, saturated or unsaturated C1-C22, in particular C2-C20, hydrocarbon-based chain, which may be substituted with a group chosen from amine groups NH2 or NHR (R being a linear or branched C1-C20, in particular C1-C6, alkyl, a C3-C40 cycloalkyl or a C6-C30 aromatic radical); the hydroxyl group (OH), a thiol group, an aryl group (more particularly benzyl), which is possibly substituted with an NH2 or NHR group; it being possible for R1 to be interrupted with a heteroatom (O, S or NH) or a carbonyl group (CO), R2 and R3, which may be identical or different, represent a linear or branched alkyl group comprising from 1 to 6 carbon atoms, y denotes an integer ranging from 0 to 3, and z denotes an integer ranging from 0 to 3, and x denotes an integer ranging from 0 to 2, with z+x+y=3.

An embodiment of the present disclosure is directed to a method for artificially coloring hair and inhibiting the coloring from fading, the method comprising:

(a) treating hair, before artificially coloring hair, with:
  i. about 0.5 wt. % to about 50 wt. % of one or more divalent metal salts of an inorganic acid; and
  ii. about 0.5 wt. % to about 50 wt. % of one or more monovalent or divalent metal salts of an organic acid; and (b) treating the hair with a hair coloring composition comprising one or more colorants chosen from oxidative dye precursors, direct dyes, pigments, and mixtures thereof;

all weights being based on the total weight of the pre-color treatment composition;

wherein the one or more divalent metal salts of an inorganic acid (i) and the one or more monovalent or divalent metal salts of an organic acid (ii) are applied together or separately onto the hair; and wherein the one or more divalent metal salts of an inorganic acid (i) and the one or more monovalent or divalent metal salts of an organic acid (ii), together or separately, are contained in a cosmetically acceptable solvent(s).

In an embodiment, the one or more divalent metal salts of an inorganic acid are chosen from calcium chloride, calcium sulfate, calcium nitrate, calcium carbonate and hydrogen carbonate, calcium phosphate, zinc chloride, zinc sulfate, zinc nitrate, zinc carbonate and hydrogen carbonate, zinc phosphate, magnesium chloride, magnesium sulfate, magnesium nitrate, magnesium carbonate and hydrogen carbonate, magnesium phosphate, strontium chloride, strontium nitrate, barium chloride, barium nitrate, and mixtures thereof.

In an embodiment, the one or more monovalent or divalent metal salts of an organic acid are chosen from metal ascorbates, formates, acetates, glycolates, gluconates, lactates, mandelates, oxalates, maleates, malonates, glyoxylates, succinates, adipates, fumarates, sebacates, citrates, tartarates, malates, tricarboxylates, glutarates, glucarates, pyrrolidone carboxylates, phenolsulfonate, salicylates, their salt derivatives thereof, salts of fatty acids having at least 10 carbon atoms, and mixtures thereof.

In an embodiment, the one or more divalent metal salts of an organic acid are chosen from zinc lactate, zinc gluconate, zinc phenolsulfonate, zinc salicylate, zinc pyrrolidone carboxylic acid (Zinc PCA), zinc citrate, zinc ascorbate, their salt derivatives thereof, and mixtures thereof.

In an embodiment, the one or more monovalent metal salts of an organic acid are chosen from sodium ascorbate, sodium formate, sodium gluconate, sodium glutamate, sodium glycolate, sodium glyoxylate, sodium citrate, sodium acetate, sodium lactate, sodium malate, sodium salicylate, potassium acetate, potassium citrate, potassium gluconate, potassium lactate, lithium myristate, lithium stearate, lithium gluconate, silver citrate, silver lactate, silver salicylate, their derivatives thereof, and mixtures thereof.

In an embodiment, the one or more monovalent metal salts of an organic acid includes a sodium salt and/or potassium salt.

In an embodiment, the pre-color treatment composition comprises one or more divalent metal salts of an inorganic acid chosen from calcium chloride, calcium sulfate, calcium nitrate, calcium carbonate and hydrogen carbonate, calcium phosphate, magnesium chloride, magnesium sulfate, magnesium nitrate, magnesium carbonate and hydrogen carbonate, magnesium phosphate, strontium chloride, strontium nitrate, barium chloride, barium nitrate, and mixtures thereof; and one or more divalent metal salts of an organic acid chosen from zinc lactate, zinc gluconate, zinc phenolsulfonate, zinc salicylate, zinc pyrrolidone carboxylic acid (Zinc PCA), zinc ascorbate, their derivatives thereof, and mixtures thereof.

In an embodiment, the pre-color treatment composition comprises one or more divalent metal salts of an inorganic acid chosen from calcium chloride and one or more divalent metal salts of an organic acid chosen from zinc gluconate.

In an embodiment of the present disclosure, the pre-color treatment composition for use in the above-described methods contains, in a cosmetically acceptable solvent:
(a) one or more divalent metal salts of an inorganic acid present in an amount of from about 0.5 wt. % to about 50 wt. % based on the total weight of the pre-color treatment composition; and
(b) one or more divalent metal salts of an organic acid present in an amount of from about 0.5 wt. % to about 50 wt. %, based on the total weight of the pre-color treatment composition.

In an embodiment, of the present disclosure, the pre-color treatment composition for use in the above-described methods contains, in a cosmetically acceptable solvent:
(a) one or more divalent metal salts of an inorganic acid chosen from calcium chloride, calcium sulfate, calcium nitrate, calcium carbonate and hydrogen carbonate, calcium phosphate, magnesium chloride, magnesium sulfate, magnesium nitrate, magnesium carbonate and hydrogen carbonate, magnesium phosphate, strontium chloride, strontium nitrate, barium chloride, barium nitrate, and mixtures thereof; and
(b) one or more monovalent or divalent metal salts of an organic acid chosen from zinc lactate, zinc gluconate, zinc phenolsulfonate, zinc salicylate, zinc pyrrolidone carboxylic acid (Zinc PCA), zinc ascorbate, sodium ascorbate, sodium formate, sodium gluconate, sodium glutamate, sodium glycolate, sodium glyoxylate, sodium citrate, sodium acetate, sodium lactate, sodium malate, sodium salicylate, potassium acetate, potassium citrate, potassium gluconate, potassium lactate, lithium myristate, lithium stearate, lithium gluconate, silver citrate, silver lactate, silver salicylate, their derivatives thereof, and mixtures thereof.

In an embodiment, the weight ratio of the one or more divalent metal salts of an inorganic acid to the one or more monovalent or divalent metal salts of an organic acid is from about 10:1 to about 1:10 or from about 8:1 to about 1:8 or from about 5:1 to about 1:5 or from about 3:1 to about 1:3 or from about 2:1 to about 1:2 or at about 1, including ranges and sub-ranges therebetween.

In an embodiment, the amount of the one or more divalent metal salts of an inorganic acid is greater than the amount of the one or more monovalent or divalent metal salts of an organic acid; for example, the weight ratio of the one or more divalent metal salts of an inorganic acid to the one or more monovalent or divalent metal salts of an organic acid can be 10:1, or 9:1, or 8:1, or 7:1, or 6:1, or 5:1, or 4;1, or 3;1, or 2:1.

In an embodiment, the amount of the one or more divalent metal salts of an inorganic acid is less than the amount of the one or more monovalent or divalent metal salts of an organic acid; for example, the weight ratio of the one or more divalent metal salts of an inorganic acid to the one or more monovalent or divalent metal salts of an organic acid can be 1:10, or 1:9, or 1:8, or 1:7, or 1:6, or 1:5, or 1:4, or 1:3, or 1:2.

In an embodiment, upon treating the hair with the pre-color treatment composition in (a), the pre-color treatment composition is allowed to remain on the hair for about 1 minute to about 1 hour or up to about 10 minutes, or up to about 20 minutes, or up to about 30 minutes, or up to about 45 minutes, at a temperature of about 20° C. to about 45° C. before treating the hair with the hair coloring composition in (b).

In embodiment, the one or more silane compounds in the post-treatment composition are chosen from 3-aminopropyltriethoxysilane (APTES), 3-aminoethyltriethoxysilane (AETES), 3-aminopropylmethyldiethoxysilane, N-(2-aminoethyl)-3-aminopropyltriethoxysilane, 3-(m-aminophenoxy)propyltrimethoxysilane, p-aminophenyltrimethoxysilane and N-(2-aminoethylaminomethyl) phenethyltrimethoxysilane, their oligomers, and mixtures thereof.

In embodiment, the one or more silane compounds in the post-treatment composition are chosen from 3-aminopropyltriethoxysilane (APTES).

In embodiment, the post-color treatment composition is applied to the colored hair within a period of time ranging from about 30 seconds, or about 1 minute, or about 5 minutes up to about 24 hours of the hair being colored.

In embodiment, the post-color treatment composition is applied to the colored hair within about one hour of the hair being colored In embodiment, the post-color treatment composition is allowed to remain on the hair for about 1 minute to about 1 hour at a temperature of about 20° C. to about 45° C.

In embodiment, the post-color treatment composition is allowed to remain on the hair for at least 5 minutes to about 30 minutes.

In an embodiment of the present disclosure, the invention is directed to a kit for artificially coloring hair, the kit comprising:
(i) a pre-color treatment component comprising one or more divalent metal salts of an inorganic acid and one or more monovalent or divalent metal salts of an organic acid;
(ii) a hair coloring composition comprising one or more colorants chosen from oxidative dye precursors, direct dyes, pigments, and mixtures thereof
(iii) an oxidizing composition comprising: (i) one or more oxidizing agents; and (ii) a cosmetically acceptable solvent chosen from water and a water/organic solvent mixture; wherein the one or more oxidizing agents are chosen from peroxides, persulfates, perborates, percarbonates, alkali metal bromates, ferricyanides, laccases, peroxidases, redox enzymes, their salts thereof, and mixtures thereof; and
(iv) a post-color treatment composition comprising from about 1 wt. % to about 30 wt. %, based on the total weight of the post-color treatment composition, of one or more silane compounds corresponding to formula (Ia):

$$R_1Si(OR_2)_z(R_3)_x(OH)_y \quad (Ia)$$

in which:

R1 is a cyclic or acyclic, linear or branched, saturated or unsaturated C1-C22, in particular C2-C20, hydrocarbon-based chain, which may be substituted with a group chosen from amine groups NH2 or NHR (R being a linear or branched C1-C20, in particular C1-C6, alkyl, a C3-C40 cycloalkyl or a C6-C30 aromatic radical); the hydroxyl group (OH), a thiol group, an aryl group (more particularly benzyl), which is possibly substituted with an NH2 or NHR group; it being possible for R1 to be interrupted with a heteroatom (O, S or NH) or a carbonyl group (CO), R2 and R3, which may be identical or different, represent a linear or branched alkyl group comprising from 1 to 6 carbon atoms, y denotes an integer ranging from 0 to 3, and z denotes an integer ranging from 0 to 3, and x denotes an integer ranging from 0 to 2, with z+x+y=3;

wherein the one or more divalent metal salts of an inorganic acid and the one or more monovalent or divalent metal salts of an organic acid are applied to the hair separately or together as a pre-color treatment composition such that the total amount of the metal salts applied onto the hair ranges from about 0.2% to about 60 wt. %, based on the total weight of the pre-color treatment composition.

The above-described hair coloring compositions further comprise one or more oxidizing agents or is capable of being mixed with an oxidizing composition comprising: (i) one or more oxidizing agents; and (ii) a cosmetically acceptable solvent chosen from water and a water/organic solvent mixture; wherein the one or more oxidizing agents are chosen from peroxides, persulfates, perborates, percarbonates, alkali metal bromates, ferricyanides, laccases, peroxidases, redox enzymes, their salts thereof, and mixtures thereof.

In an embodiment, pre-color treatment composition of the present invention further comprises:

one or more of a thickening agent chosen from cellulose and cellulose derivatives, starch and starch derivatives, acrylic or acrlyates based polymers, gums, and mixtures thereof;

a cationic agent chosen from cationic surfactants;

a surfactant chosen from alkoxylated fatty alcohols, fatty alcohols, and mixtures thereof, preferably chosen from fatty alcohols;

a silicone chosen from amino silicones, non-amino silicones, and mixtures thereof; preferably chosen from amino silicones; and a cosmetically acceptable solvent.

In an embodiment, post-color treatment composition of the present invention further comprises:

one or more of a thickening agent chosen from cellulose and cellulose derivatives, starch and starch derivatives, acrylic or acrlyates based polymers, gums, and mixtures thereof;

a surfactant chosen from alkoxylated fatty alcohols, fatty alcohols, and mixtures thereof, preferably, chosen from alkoxylated fatty alcohols;

optionally, a silicone chosen from amino silicones, non-amino silicones, and mixtures thereof; and a cosmetically acceptable solvent.

It has now been surprisingly and unexpectedly discovered that the use of the compositions, methods, and kits of the present disclosure resulted in good deposit of artificial color onto hair as well as durable artificial color wherein the fading of the artificial was found to be minimal even over several shampooings of the hair.

Divalent Metal Salts of an Inorganic Acid

The one or more divalent metal salts of an inorganic acid may be chosen from metal halides, metal hydroxides, metal sulfates, metal oxides, and mixtures thereof.

The divalent metals with which the metal salts are formed are calcium, zinc, iron, nickel, copper, silver, magnesium, strontium, barium, manganese, cobalt, and mixtures thereof.

Suitable examples of the one or more divalent metal salts of an inorganic acid may be chosen from calcium chloride, calcium sulfate, calcium nitrate, calcium carbonate and hydrogen carbonate, calcium phosphate, zinc chloride, zinc sulfate, zinc nitrate, zinc carbonate and hydrogen carbonate, zinc phosphate, magnesium chloride, magnesium sulfate, magnesium nitrate, magnesium carbonate and hydrogen carbonate, magnesium phosphate, strontium chloride, strontium nitrate, barium chloride, barium nitrate, and mixtures thereof.

In an embodiment, the one or more divalent metal salts of an inorganic acid includes a calcium salt.

In an embodiment, the calcium salt is calcium chloride.

The one or more divalent metal salts of an inorganic acid may be present in the hair coloring compositions of the present disclosure in an amount of from about 0.1 wt. % to about 50 wt. % or from about 0.2 wt. % to about 45 wt. % or from about 0.3 wt. % to about 45 wt. % or from about 0.5 wt. % to about 40 wt. % or from about 1 wt. % to about 40 wt. %, or from about 1.5 wt. % to about 35 wt. %, or from about 2 wt. % to about 30 wt. %, or from about 2.5 wt. % to about 30 wt. %, including all ranges and sub-ranges therebetween, based on the total weight of the hair coloring composition.

In various embodiments, the one or more divalent metal salts of an inorganic acid is present in the hair coloring compositions of the present disclosure in a wt. % amount of about 0.1, 0.2, 0.3, 0.4, 0.5, 0.75, 1, 1.25, 1.5, 1.75, 2, 2.25, 2.5, 2.75, 3, 3.25, 3.5, 3.75, 4, 4.25, 4.5, 4.75, 5, 5.25, 5.5, 5.75, 6.25, 6.5, 6.75, 7, 7.25, 7.5, 7.75, 8, 8.25, 8.5, 8.75, 9, 9.25, 9.5, 9.75, 10, 11, 12, 14, 15, 16, 18, 20, 22, 24, 25, 26, 28, 30, 32, 34, 35, 36, 38, 40, 42, 44, 45, 46, 48, or 50 wt. %, based on the total weight of the hair coloring composition.

Monovalent or Divalent Metal Salts of an Organic Acid

The one or more monovalent or divalent metal salts of an organic acid may be chosen from metal salts wherein the organic acid is chosen from C1 to C9 monocarboxylic or di-carboxylic acids, polycarboxylic acids, hydroxy-carboxylic acids, and fatty acids having at least 10 carbon atoms including ascorbic acid, formic acid, acetic acid, glycolic acid, gluconic acid, lactic acid, mandelic acid, oxalic acid, maleic acid, malonic acid, glyoxylic acid, succinic acid, adipic acid, fumaric acid, sebacic acid, including citric acid, tartaric acid, malic acid, 2-hydroxy malonic acid, 2-hydroxyl n-butyl 1,2,4-tricarboxylic acid, glutaric acid, glucaric acid, 2-hydroxy n-butyl 1,3,4-tricarboxylic acid, pyrrolidone carboxylic acid, phenolsulfonic acid, and salicylic acid.

Suitable examples monovalent or divalent metal salts of an organic acid are chosen from metal ascorbates, formates, acetates, glycolates, gluconates, lactates, mandelates, oxalates, maleates, malonates, glyoxylates, succinates, adipates, fumarates, sebacates, citrates, tartarates, malates, tricarboxylates, glutarates, glucarates, pyrrolidone carboxylates, phenolsulfonate, salicylates, their salt derivatives thereof, salts of fatty acids having at least 10 carbon atoms, and mixtures thereof.

In an embodiment, the one or more divalent metal salts of an organic acid are chosen from zinc lactate, zinc gluconate, zinc phenolsulfonate, zinc salicylate, zinc pyrrolidone carboxylic acid (Zinc PCA), zinc ascorbate, zinc citrate, their salt derivatives thereof, and mixtures thereof.

In an embodiment, the one or more divalent metal salts of an organic acid includes a zinc salt.

In an embodiment, the zinc salt is zinc gluconate.

In an embodiment, the one or more monovalent metal salts of an organic acid are chosen from sodium ascorbate, sodium formate, sodium gluconate, sodium glutamate, sodium glycolate, sodium glyoxylate, sodium citrate, sodium acetate, sodium lactate, sodium malate, sodium salicylate, potassium acetate, potassium citrate, potassium gluconate, potassium lactate, lithium myristate, lithium stearate, lithium gluconate, silver citrate, silver lactate, silver salicylate, their derivatives thereof, and mixtures thereof.

In an embodiment, the one or more monovalent metal salts of an organic acid includes a sodium salt and/or potassium salt.

The one or more monovalent or divalent metal salts of an organic acid may be present in the hair coloring compositions of the present disclosure in an amount of from 0.1 wt. % to about 50 wt. % or from about 0.2 wt. % to about 45 wt. % or from about 0.3 wt. % to about 45 wt. % or from about 0.5 wt. % to about 40 wt. % or from about 1 wt. % to about 40 wt. %, or from about 1.5 wt. % to about 35 wt. %, or from about 1.75 wt. % to about 35 wt. %, or from about 2.5 wt. % to about 30 wt. %, or from about 2 wt. % to about 30 wt. %, or from about 2.5 wt. % to about 25 wt. %, or from about 3 wt. % to about 20 wt. %, or from about 4 wt. % to about 15 wt. %, or from about 5 wt. % to about 10 wt. %, including all ranges and sub-ranges therebetween, based on the total weight of the hair coloring composition.

In various embodiments, the one or more monovalent or divalent metal salts of an organic acid is present in the hair coloring compositions of the present disclosure in a wt. % amount of about 0.1, 0.2, 0.3, 0.4, 0.5, 0.75, 1, 1.25, 1.5, 1.75, 2, 2.25, 2.5, 2.75, 3, 3.25, 3.5, 3.75, 4, 4.25, 4.5, 4.75, 5, 5.25, 5.5, 5.75, 6.25, 6.5, 6.75, 7, 7.25, 7.5, 7.75, 8, 8.25, 8.5, 8.75, 9, 9.25, 9.5, 9.75, 10, 11, 12, 14, 15, 16, 18, 20, 22, 24, 25, 26, 28, 30, 32, 34, 35, 36, 38, 40, 42, 44, 45, 46, 48, or 50 wt. %, based on the total weight of the hair coloring composition.

Cosmetically Acceptable Solvent (or Carrier)

The compositions of the present disclosure may be presented in a cosmetically acceptable solvent. This cosmetically acceptable solvent may include, for example, water or a mixture of water and at least one cosmetically acceptable organic solvent.

As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol.

Other suitable examples of organic solvents are ethylene glycol, propylene glycol, butylene glycol, hexylene glycol, propane diol, and glycerin.

The organic solvents for use in the present disclosure can be volatile or non-volatile compounds.

The cosmetically acceptable solvent may be employed according to the present disclosure in an amount ranging from about 5% to about 95% by weight, or such as from about 20% to about 90% by weight, such as from about 30 to about 80% by weight, or such as from about 35% to about 75% by weight, such as from about 5 to about 50% by weight, such as from about 50 to 95% by weight, based on the total weight of the composition.

The organic solvent may be employed according to the present disclosure in an amount ranging from about 0.1% to about 25% by weight, such as from about 1% to about 15% by weight, or such as from about 3% to about 10% by weight, or such as from about 5% to about 10% by weight, based on the total weight of the composition of the present disclosure.

Colorants

The coloring compositions of the present disclosure include at least one colorant compound chosen from oxidative dye precursors, direct dyes, pigments, and mixtures thereof. The oxidation dyes are generally chosen from one or more oxidation bases optionally combined with one or more couplers. By way of example, the oxidation bases are chosen from para-phenylenediamines, bis(phenyl)alkylenediamines, para-aminophenols, ortho-aminophenols and heterocyclic bases, and the addition salts thereof.

Among the para-phenylenediamines that may be mentioned, for example, are para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N, N-dimethyl-para-phenylenediamine, N,N-diethyl-para-phenylenediamine, N,N-dipropyl-para-phenylenediamine, 4-amino-N,N-diethyl-3-methylaniline, N,N-bis(.beta.-hydroxyethyl)-para-phenylenediamine, 4-N, N-bis(.beta.-hydroxyethyl)amino-2-methylaniline, 4-N,N-bis(.beta.-hydroxyethyl)amino-2-chloroaniline, 2-.beta.-hydroxyethyl-para-phenylenediamine, 2-methoxymethyl-para-phenylenediamine, 2-fluoro-para-phenylenediamine, 2-isopropyl-para-phenylenediamine, N-(.beta.-hydroxypropyl)-para-phenylenediamine, 2-hydroxymethyl-para-phenylenediamine, N,N-dimethyl-3-methyl-para-phenylenediamine, N-ethyl-N-(.beta.-hydroxyethyl)-para-phenylenediamine, N-(.beta.,.gamma.-dihydroxypropyl)-para-phenylenediamine, N-(4'-aminophenyl)-para-phenylenediamine, N-phenyl-para-phenylenediamine, 2-.beta.-hydroxyethyoxy-para-phenylenediamine, 2-.beta.-acetylaminoethyloxy-para-phenylenediamine, N-(.beta.-methoxyethyl)-para-phenylenediamine, 4-aminophenylpyrrolidine, 2-thienyl-para-phenylenediamine, 2-.beta.-hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine, para-toluenediamine, 2-isopropyl-para-phenylenediamine, 2-.beta.-hydroxyethyl-para-phenylenediamine, 2-.beta.-hydroxyethyoxy-para-phenylenediamine, 2,6-dimethyl-para-phenylenediamine, 2,6-diethyl-para-phenylenediamine, 2,3-dimethyl-para-phenylenediamine, N,N-bis(.beta.-hydroxyethyl)-para-phenylenediamine, 2-chloro-para-phenylenediamine and 2-.beta.-acetylaminoethyloxy-para-phenylenediamine, and the addition salts thereof with an acid, are particularly preferred.

Among the bis(phenyl)alkylenediamines that may be mentioned, for example, are N,N'-bis(.beta.-hydroxyethyl)-N,N'-bis(4'-aminophenyl)-1,3-diaminopropano-I, N,N'-bis(.beta.-hydroxyethyl)-N,N'-bis(4'-aminophenyl)ethylenediamine, N,N'-bis(4-aminophenyl)tetramethylenediamine, N,N'-bis(.beta.-hydroxyethyl)-N,N'-bis(4-aminophenyl)tetramethylenediamin-e, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(.beta.-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

Among the heterocyclic bases that may be mentioned, for example, are pyridine derivatives, pyrimidine derivatives and pyrazole derivatives.

Among the pyridine derivatives that may be mentioned are the compounds such as 2,5-diaminopyridine, 2-(4-methoxyphenyl)amino-3-aminopyridine and 3,4-diaminopyridine, and the addition salts thereof. Other pyridine oxidation bases that are useful in the present disclosure are the 3-aminopyrazolo[1,5-a]pyridine oxidation bases or the addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-.quadrature.-hydroxyethoxy-3-amino-pyrazolo[1,5-a]pyridine; 2-(4-dimethylpyperazinium-1-yl)-3-amino-pyrazolo[1,5-a]pyridine; and the addition salts thereof.

More particularly oxidation bases that are useful in the present disclosure are selected from 3-aminopyrazolo-[1,5-a]-pyridines and preferably substituted on carbon atom 2 by:
(a) one (di)($C_1$-$C_6$)(alkyl)amino group wherein said alkyl group can be substituted by at least one hydroxy, amino, imidazolium group;
(b) one heterocycloalkyl group containing from 5 to 7 members chain, and from 1 to 3 heteroatoms, potentially cationic, potentially substituted by one or more ($C_1$-$C_6$-alkyl, such as di(C1-C4)alkylpiperazinium; or
(c) one ($C_1$-$C_6$)alkoxy potentially substituted by one or more hydroxy groups such as .quadrature.-hydroxyalkoxy, and the addition salts thereof.

Among the pyrimidine derivatives that may be mentioned are compounds such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and their addition salts and their tautomeric forms, when a tautomeric equilibrium exists.

Among the pyrazole derivatives that may be mentioned are compounds such as 4,5-diamino-1-methyl-pyrazole, 4,5-diamino-1-(.beta.-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenyl-pyrazole, 4,5-diamino-1-methyl-3-phenylpyrazole, 4-amino-1,3-dimethyl-5-hydrazinopyrazole, 1-benzyl-4,5-diamino-3-methyl-pyrazole, 4,5-diamino-3-tert-butyl-1-methylpyrazole, 4,5-diamino-1-tert-butyl-3-methylpyrazole, 4,5-diamino-1-(.beta.-hydroxyethyl)-3-methylpyrazole, 4,5-diamino-1-ethyl-3-methyl-pyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(.beta.-hydroxyethyl)amino-1-methylpyrazole, and the addition salts thereof. 4,5-Diamino-1-(.beta.-methoxyethyl)pyrazole may also be used.

Pyrazole derivatives that may also be mentioned include diamino-N,N-dihydropyrazolopyrazolones such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-on-e, 4,5-diamino-1,2-dimethyl-1,2-dihydropyrazol-3-one, 4,5-diamino-1,2-diethyl-1,2-dihydropyrazol-3-one, 4,5-diamino-1,2-di-(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-o-ne. 2,3-Diamino-6,7-dihydro-1H,5H-pyrazolo[1,2-a]pyrazol-1-one and/or a salt thereof will preferably be used. 4,5-Diamino-1-(.beta.-hydroxyethyl)pyrazole and/or 2,3-diamino-6,7-dihydro-1H,5H-pyrazolo[1,2-a]pyrazol-1-one and/or a salt thereof will preferentially be used as heterocyclic bases.

Composition according to the present disclosure may optionally comprise one or more couplers advantageously chosen from those conventionally used in the dyeing or coloring of keratin fibers.

Among these couplers, mention may be made especially of meta-phenylenediamines, meta-aminophenols, meta-diphenols, naphthalene-based couplers and heterocyclic couplers, and also the addition salts thereof.

Mention may be made, for example, of 2-methyl-5-aminophenol, 5-N-(.beta.-hydroxyethyl)amino-2-methylphenol, 3-aminophenol, 5-amino-6-chloro-o-cresol (3-amino-2-chloro-6-methylphenol), 1,3-dihydroxybenzene, 1,3-dihydroxy-2-methyl-benzene, 4-chloro-1,3-dihydroxybenzene, 2,4-diamino-1-(.beta.-hydroxyethyl oxy) benzene, 2-amino-4-(.beta.-hydroxyethylamino)-1-methoxybenzene, 1,3-diaminobenzene, 1,3-bis(2,4-diamino-phenoxy)propane, 3-ureidoaniline, 3-ureido-1-dimethylamino-benzene, sesamol, 1-.beta.-hydroxyethylamino-3,4-methylene-dioxybenzene, .alpha.-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(.beta.-hydroxyethyl)amino-3,4-methylene-dioxybenzene, 2,6-bis(J-hydroxyethylamino) toluene, 6-hydroxy-indoline, 2,6-dihydroxy-4-methylpyridine, 1-H-3-methyl pyrazol-5-one, 1-phenyl-3-methylpyrazol-5-one, 2,6-dimethyl-pyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

In general, the addition salts of the oxidation bases and couplers that may be used in the context of the disclosure are especially selected from the addition salts with an acid such as the hydrochlorides, hydrobromides, sulfates, citrates, succinates, tartrates, lactates, tosylates, benzenesulfonates, phosphates and acetates.

The oxidation base(s) each advantageously represent from 0.001% to 10% by weight relative to the total weight of the composition, and preferably from 0.005% to 5% by weight relative to the total weight of the compositions of the present disclosure.

The coupler(s), if they are present, each advantageously represent from 0.001% to 10% by weight relative to the total weight of the composition, and preferably from 0.005% to 5% by weight relative to the total weight of the compositions of the present disclosure.

Compositions according to the disclosure may optionally comprise b) one or more synthetic or natural direct dyes, chosen from anionic and nonionic species, preferably cationic or nonionic species, either as sole dyes or in addition to the oxidation dye(s).

Examples of suitable direct dyes that may be mentioned include azo direct dyes; (poly)methine dyes such as cyanins, hemicyanins and styryls; carbonyl dyes; azine dyes; nitro (hetero)aryl dyes; tri(hetero)arylmethane dyes; porphyrin dyes; phthalocyanin dyes, and natural direct dyes, alone or as mixtures.

Many direct dyes are cationic direct dyes. Mention may be made of the hydrazono cationic dyes of formulas (Va) and (V'a), the azo cationic dyes (VIa) and (VI'a) and the diazo cationic dyes (VIIa) below:

Het$^+$-C(R$^a$)=N—N(R$^b$)—Ar, An$^-$ (Va)

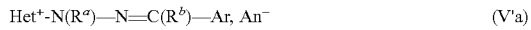

Het$^+$-N(R$^a$)—N=C(R$^b$)—Ar, An$^-$ (V'a)

Het$^+$-N=N—Ar, An$^-$ (VIa)

Ar$^+$—N=N—Ar'', An$^-$ (VI'a) and

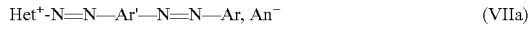

Het$^+$-N=N—Ar'—N=N—Ar, An$^-$ (VIIa)

in which formulas (Va), (V'a), (VIa), (VI'a) and (VIIa):

Het$^+$ represents a cationic heteroaryl radical, preferably bearing an endocyclic cationic charge, such as imidazolium, indolium or pyridinium, optionally substituted preferentially with one or more (C$_1$-C$_8$) alkyl groups such as methyl;

Ar$^+$ representing an aryl radical, such as phenyl or naphthyl, bearing an exocyclic cationic charge, preferably ammonium, particularly tri(C$_1$-C$_8$)alkylammonium such as trimethylammonium;

Ar represents an aryl group, especially phenyl, which is optionally substituted, preferentially with one or more electron-donating groups such as i) optionally substituted (C$_1$-C$_8$)alkyl, ii) optionally substituted (C$_1$-C$_8$)alkoxy, iii) (di) (C$_1$-C$_8$)(alkyl)amino optionally substituted on the alkyl group(s) with a hydroxyl group, iv) aryl(C$_1$-C$_8$)alkylamino, v) optionally substituted N—(C$_1$-C$_8$)alkyl-N-aryl(C$_1$-C$_8$) alkylamino or alternatively Ar represents a julolidine group;

Ar' is an optionally substituted divalent (hetero)arylene group such as phenylene, particularly para-phenylene, or naphthalene, which are optionally substituted, preferentially with one or more groups (C$_1$-C$_8$)alkyl, hydroxyl or (C$_1$-C$_8$) alkoxy Ar'' is an optionally substituted (hetero)aryl group such as phenyl or pyrazolyl, which are optionally substituted, preferentially with one or more groups (C$_1$-C$_8$)alkyl, hydroxyl, (di)(C$_1$-C$_8$)(alkyl)amino, (C$_1$-C$_8$)alkoxy or phenyl;

R$^a$ and R$^b$, which may be identical or different, represent a hydrogen atom or a group (C$_1$-C$_8$)alkyl, which is optionally substituted, preferentially with a hydroxyl group;

or alternatively the substituent R$^a$ with a substituent of Het$^+$ and/or R$_b$ with a substituent of Ar and/or R$^a$ with R$_b$ form, together with the atoms that bear them, a (hetero) cycloalkyl;

particularly, R$^a$ and R$_b$ represent a hydrogen atom or a group (C$_1$-C$_4$)alkyl, which is optionally substituted with a hydroxyl group;

An$^-$ represents an anionic counter-ion such as mesylate or halide. In particular, mention may be made of the azo and hydrazono cationic dyes bearing an endocyclic cationic charge of formulae (Va), (V'a) and (VIa) as defined previously. More particularly those of formulae (Va), (V'a) and (VIa) derived from the dyes described in patent applications WO 95/15144, WO 95/01772 and EP-714954, which are incorporated herein by reference in their entirety.

In some cases, the cationic part is derived from the following derivatives:

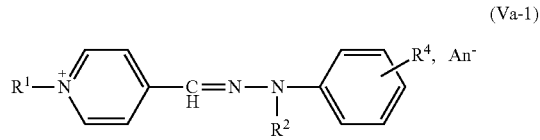

(Va-1)

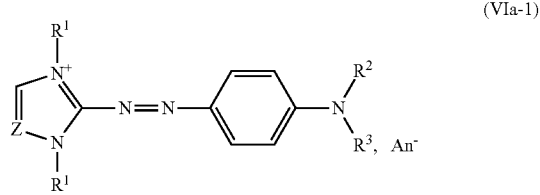

(VIa-1)

formulae (V-1) and (V1-1) with:

R$^1$ representing a (C$_1$-C$_4$) alkyl group such as methyl;

R$^2$ and R$^3$, which are identical or different, represent a hydrogen atom or a (C$_1$-C$_4$)alkyl group, such as methyl; and R$^4$ represents a hydrogen atom or an electron-donating group such as optionally substituted (C$_1$-C$_8$)alkyl, optionally substituted (C$_1$-C$_8$)alkoxy, or (di)(C$_r$ C$_8$)(alkyl)amino optionally substituted on the alkyl group(s) with a hydroxyl group; particularly, R$^4$ is a hydrogen atom, Z represents a CH group or a nitrogen atom, preferentially CH;

An$^-$ represents an anionic counter-ion such as mesylate or halide.

Particularly, the dye of formulae (Va-1) and (VIa-1) is chosen from Basic Red 51, Basic Yellow 87 and Basic Orange 31 or derivatives thereof:

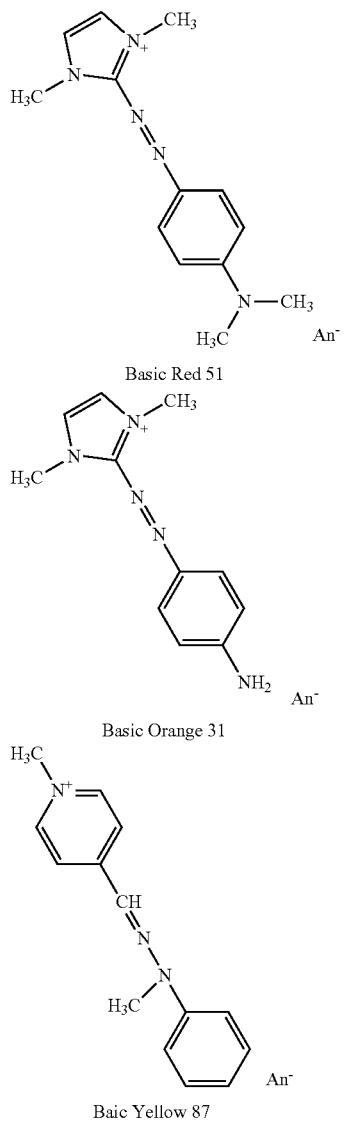

Basic Red 51

Basic Orange 31

Baic Yellow 87

Among the natural direct dyes that may be used according to the disclosure, mention may be made of lawsone, juglone, alizarin, purpurin, carminic acid, kermesic acid, purpurogallin, protocatechaldehyde, indigo, isatin, curcumin, spinulosin, apigenidin and orceins. Extracts or decoctions containing these natural dyes and in particular henna-based poultices or extracts may also be used.

When they are present, the direct dye(s) more particularly represent from 0.001% to 10% by weight and preferably from 0.005% to 5% by weight of the total weight of the compositions of the present disclosure.

Alkalizing Agents

The hair coloring composition may have a pH that is alkaline. Exemplary pH's include 7, 8, 9, 10, 11, 12, 13 or 14. In some embodiments, the pH of the hair coloring composition may range from about 7, 8, or 9 to about 9, 10, 11 or 12.

The alkalinity of the hair coloring composition may be derived from one or more alkalizing agents. In some embodiments, the alkalizing agent may ammonia or an ammonia gas-generating compound and/or an amine or ammonium-based compound in amounts sufficient to make such compositions alkaline. In further embodiments, the alkalizing agent may be selected from alkanolamines, such as monoethanolamine (MEA) and isopropanolamine. Alkalinity may be derived from ammonium compounds as well (e.g., NH4OH).

The one or more alkalizing agents may be present in amounts ranging from greater than about 0, or from 1, 2, 3, 4, 5, 10 to about 5, 10, 13, 15, 18, 20, 25 or 30% by weight of the total composition.

Oxidizing Agents

Oxidizing agents may be selected from, for example, peroxides, persulfates, perborates percarbonates, alkali metal bromates, ferricyanides, peroxygenated salts, or mixtures thereof. Oxidizing agents that may also be used include at least one redox enzyme such as laccases, peroxidases, and 2-electron oxidoreductases, such as uricase, where appropriate in the presence of their respective donor or co-factor. Oxygen in the air may also be employed as an oxidizing agent.

In some cases, the oxidizing agent is hydrogen peroxide present in an aqueous solution whose titre may range from 1 to 40 volumes, such as from 5 to 40 volumes or such as from 5 to 20 volumes.

In other cases, the oxidizing agent is a persulfate and/or a monopersulfate such as, for example, potassium persulfate, sodium persulfate, ammonium persulfate, as well as mixtures thereof. In one embodiment, the oxidizing agents in the present disclosure are selected from hydrogen peroxide, potassium persulfate, sodium persulfate, and mixtures thereof. Hydrogen peroxide may commonly be used as the oxidizing agent.

In an embodiment, the oxidizing agent is hydrogen peroxide and is provided as an oxidizing (developer) composition.

In general, the oxidizing agent will be present in an amount of from about 0.05 to about 50% by weight, such as from about 0.1% to about 30% by weight, or such as from about 0.1% to about 20% by weight, or such as from about 1% to about 10% by weight, based on the total weight of the oxidizing composition.

In some instances, the oxidizing composition is aqueous or is in the form of an emulsion.

In other instances, the oxidizing composition is substantially anhydrous. The term "substantially anhydrous" means that the oxidizing composition is either completely free of water or contains no appreciable amount of water, for example, no more than 5% by weight, or no more than 2% by weight, or no more than 1% by weight, based on the weight of the oxidizing composition. It should be noted that this refers for example to bound water, such as the water of crystallization of the salts or traces of water absorbed by the raw materials used in the preparation of the compositions according to the disclosure.

The oxidizing composition can contain at least one solvent, chosen from water, organic solvents, and mixtures thereof. When the oxidizing composition is substantially anhydrous, the oxidizing composition may comprise at least one solvent chosen from organic solvents. Suitable organic solvents for use in the oxidizing composition include ethanol, isopropyl alcohol, propanol, benzyl alcohol, phenyl ethyl alcohol, glycols and glycol ethers, such as propylene glycol, hexylene glycol, ethylene glycol monomethyl, monoethyl or monobutyl ether, propylene glycol and its ethers, such as propylene glycol monomethyl ether, butylene glycol, dipropylene glycol, diethylene glycol alkyl ethers, such as diethylene glycol monoethyl ether and monobutyl ether, ethylene glycol, propylene glycol, butylene glycol, hexylene glycol, propane diol, glycerin, hydrocarbons such as straight chain hydrocarbons, mineral oil, polybutene, hydrogenated polyisobutene, hydrogenated polydecene, polydecene, squalane, petrolatum, isoparaffins, and mixtures, thereof.

The organic solvent may, for example, be present in an amount ranging from about 0.5% to about 70% by weight, such as from about 2% to about 60% by weight, preferably from about 5 to about 50% by weight, relative to the total weight of the oxidizing composition.

The oxidizing composition may be in the form of a powder, gel, liquid, foam, lotion, cream, mousse, and emulsion.

The oxidizing composition of the present disclosure my also contain at least one fatty substance as described above. Thus, the total amount of fatty substances in the combination or mixture of the coloring and oxidizing compositions of the present disclosure may range from about 10% to about 80% by weight, or such as from about 20% to about 60% by weight, or such as from about 20% to about 40% by weight, or such as from about 20% to about 30% by weight, based on the total weight of the composition.

Silane Compound

According to the invention, the post-color treatment composition comprises one or more silane compound corresponding to formula (Ia) and/or its oligomers and/or polymers thereof.

Formula (Ia) is as follows:

in which:
- $R_1$ is a cyclic or acyclic, linear or branched, saturated or unsaturated $C_1$-$C_{22}$, in particular $C_2$-$C_{20}$, hydrocarbon-based chain, which may be substituted with a group chosen from amine groups $NH_2$ or NHR (R being a linear or branched $C_1$-$C_{20}$, in particular $C_1$-$C_6$, alkyl, a $C_3$-$C_{40}$ cycloalkyl or a $C_6$-$C_{30}$ aromatic radical); the hydroxyl group (OH), a thiol group, an aryl group (more particularly benzyl), which is possibly substituted with an $NH_2$ or NHR group; it being possible for R1 to be interrupted with a heteroatom (O, S or NH) or a carbonyl group (CO),
- $R_2$ and $R_3$, which may be identical or different, represent a linear or branched alkyl group comprising from 1 to 6 carbon atoms,
- y denotes an integer ranging from 0 to 3, and
- z denotes an integer ranging from 0 to 3, and
- x denotes an integer ranging from 0 to 2, with z+x+y=3.

Preferably, $R_1$ is a linear or branched, preferably linear, saturated $C_1$-$C_{22}$, in particular $C_2$-$C_{12}$, hydrocarbon-based chain, which may be substituted with an amine group $NH_2$ or NHR (R=$C_1$-$C_{20}$, in particular $C_1$-$C_6$, alkyl).

Preferably, R2 represents an alkyl group comprising from 1 to 4 carbon atoms, better still a linear alkyl group comprising from 1 to 4 carbon atoms, and preferably the ethyl group.

Preferably, z ranges from 1 to 3.
Preferably, y=0.
Preferentially, z=3, and therefore x=y=0.
In one embodiment of the invention, R1 represents a linear alkyl group comprising from 7 to 18 carbon atoms and more particularly from 7 to 12 carbon atoms, or a C1-C6, preferably C2-C4, aminoalkyl group. More particularly, R1 represents an octyl group.

In one embodiment of the invention, R1 is a linear or branched, saturated or unsaturated C1-C22 hydrocarbon-based chain, substituted with an amine group NH2 or NHR (R=C1-C20, in particular C1-C6, alkyl, C3-C40 cycloalkyl or C6-C30 aromatic). In this variant, R1 preferably represents a C1-C6, preferably C2-C4, aminoalkyl group.

Preferably, the silane compound of the present invention is an alkoxysilane.

Preferably, the composition comprises at least one compound of formula (Ib) chosen from alkoxysilanes such as 3-aminopropyltriethoxysilane (APTES), 3-aminoethyltriethoxysi lane (AETES), 3-aminopropylmethyldiethoxysilane, N-(2-aminoethyl)-3-aminopropyltriethoxysilane, 3-(m-aminophenoxy)propyltrimethoxysilane, p-aminophenyltrimethoxysilane, N-(2-aminoethylaminomethyl)phenethyltrimethoxysilane, and mixtures thereof.

In certain embodiments, the siliane of the disclosure is an alkoxysilane selected from 3-aminopropyltriethoxysilane (APTES), 3-aminoethyltriethoxysilane (AETES), 3-aminopropylmethyldiethoxysilane and N-(2-aminoethyl)-3-aminopropyltriethoxysilane or oligomers thereof, and mixtures thereof.

In preferred embodiments, the silane compound of the present invention is chosen from 3-aminopropyltriethoxysilane (APTES) or oligomers thereof, or mixtures thereof.

The silane compound used in the composition of the invention, in particular those comprising a basic function, may be partially or totally neutralised. In particular, the neutralising agent may be chosen from organic or inorganic acids, such as citric acid, tartaric acid, lactic acid or hydrochloric acid, preferably, lactic acid.

Preferably, the optionally neutralised silanes according to the invention are water-soluble and in particular soluble at a concentration of 2%, better still at a concentration of 5% and even better still at a concentration of 10% and above by weight in water at a temperature of 25° C. and at atmospheric pressure (1 atm). The term "soluble" is intended to mean the formation of a single macroscopic phase.

The silane(s) of formula (Ia) and/or oligomers and/or polymers thereof may be present in the post-color treatment composition according to the invention in an amount of about 1% to about 30% by weight, such as from about 1% to about 20% by weight, from about 1.5% to about 15% by weight, from about 2% to about 14% by weight, from about 3% to about 12% by weight, from about 4% to about 10% by weight, from about 5% to about 10%, or from about 6% to less than 10%, such as from about 8% to about 10%, by weight of active material, based on the total weight of the composition, including all ranges and subranges therebetween.

In various embodiments, the total amount of the silane(s) of formula (I) is about 1%, 1.25%, 1.5%, 1.75%, 2%, 2.25%, 2.5%, 2.75%, 3%, 3.5%, 4%, 4.5%, 5%, 5.%, 6%, 6.5%, 7%, 7.5%, 8%, 8.5%, 9%, 9.5%, or 10% by weight of active material, based on the total weight of the composition.

Auxiliary Agents

Auxiliary ingredients may be added to the pre-treatment, post-treatment, hair coloring and/or oxidizing (developer) compositions of the present disclosure. Exemplary auxiliary ingredients useful according to various embodiments of the disclosure include, but are not limited to, thickening agents (including rheology-modifying and viscosity modifying agents agents), cationic agents (including cationic surfactants and cationic polymers), anionic, non-ionic and/or amphoteric/zwitterionic surfactants, bleach activators and co-bleach activators, chelants, fatty substances, ceramides, silicones, and lift-enhancing agents, such as nitrogen-containing compounds and metal catalyst compounds, and preservatives.

The compositions may also contain acid and alkali pH adjusters, which are well known in the art in the cosmetic treatment of keratin fibers, such as hair. Such pH adjusters include, but are not limited to, sodium metasilicate, silicate compounds, citric acid, ascorbic acid, and carbonate compounds.

Thickening Agents

The compositions of the present disclosure may contain one or more thickening agents which include rheology or viscosity modifying agents, such as viscosity increasing agents. Classes of such agents include, but are not limited to, viscous liquids, such as polyethylene glycol, thickening polymers, such as cellulose derivatives (for example, hydroxyethyl cellulose, hydroxypropyl methylcellulose), and acrylic acid and/or acrylate based polymers (for example, carbomers, Carbopol and Pemulen types), poloxamers, and polyethyleneimines (e.g., PEI-10), naturally occurring polymers, such as acacia, tragacanth, alginates (e.g., sodium alginate), carrageenan, vegetable gums, such as xanthan gum, petroleum jelly, waxes, starches and starch derivatives such as hydroxypropyl starch phosphate, particulate associate colloids and clays/silicate clays, such as bentonite, laponite, colloidal silicon dioxide, and microcrystalline cellulose, and salts, such as sodium chloride, and mixtures thereof.

The thickening agents may, for example, be present in an amount ranging from about 0.1% to about 20% by weight, such as from about 0.2% to about 15% by weight, or from about 0.3% to about 10% by weight, or from about 0.4% to about 8% by weight, or from about 0.5% to about 6% by weight, based on the total weight of the compositions of the present disclosure.

Cationic Agents

The various compositions described herein may include one or more cationic agents such as cationic surfactants and cationic polymers.

Cationic Surfactants

The term "cationic surfactant" means a surfactant that is positively charged when it is contained in the composition according to the disclosure. This surfactant may bear one or more positive permanent charges or may contain one or more functions that are cationizable in the composition according to the disclosure.

Non-limiting examples of cationic surfactants include behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride(Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

The cationic surfactant(s) may be chosen from optionally polyoxyalkylenated, primary, secondary or tertiary fatty amines, or salts thereof, and quaternary ammonium salts, and mixtures thereof.

The fatty amines generally comprise at least one C8-C30 hydrocarbon-based chain.

Examples of quaternary ammonium salts that may especially be mentioned include: those corresponding to the general formula (A) below:

(A)

in which the groups R8 to R11, which may be identical or different, represent a linear or branched, saturated or unsaturated aliphatic group comprising from 1 to 30 carbon atoms, or an aromatic group such as aryl or alkylaryl, at least one of the groups R8 to R11 denoting a group comprising from 8 to 30 carbon atoms and preferably from 12 to 24 carbon atoms. The aliphatic groups may comprise heteroatoms especially such as oxygen, nitrogen, sulfur and halogens. The aliphatic groups are chosen, for example, from C1-C30 alkyl, C2-C30 alkenyl, C1-C30 alkoxy, polyoxy(C2-C6) alkylene, C1-C30 alkyl amide, (C12-C22)alkylamido(C2-C6)alkyl, (C12-C22)alkyl acetate and C1-C30 hydroxyalkyl groups; X– is an anion chosen from the group of halides, phosphates, acetates, lactates, (C1-C4)alkyl sulfates, and (C1-C4)alkyl- or (C1-C4)alkylarylsulfonates.

Among the quaternary ammonium salts of formula (A), those that are preferred are, on the one hand, tetraalkylammonium salts, for instance dialkyldimethylammonium or alkyltrimethylammonium salts in which the alkyl group contains approximately from 12 to 22 carbon atoms, in particular behenyltrimethylammonium, distearyldimethylammonium, cetyltrimethylammonium or benzyldimethylstearylammonium salts, or, on the other hand, oleocetyldimethylhydroxyethylammonium salts, palmitylamidopropyltrimethylammonium salts, stearamidopropyltrimethylammonium salts and stearamidopropyldimethylcetearylammonium salts.

In some cases it is useful to use salts such as the chloride salts of the following compounds:

A. a quaternary ammonium salt of imidazoline, such as, for example, those of formula (B) below:

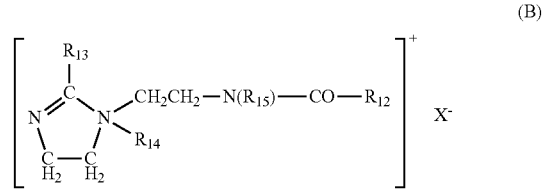

(B)

in which $R_{12}$ represents an alkenyl or alkyl group comprising from 8 to 30 carbon atoms, derived for example from tallow fatty acids, $R_{13}$ represents a hydrogen atom, a $C_1$-$C_4$ alkyl group or an alkyl or alkenyl group comprising from 8 to 30 carbon atoms, $R_{14}$ represents a $C_1$-$C_4$ alkyl group, $R_{15}$ represents a hydrogen atom or a $C_1$-$C_4$ alkyl group, X– is an anion chosen from the group of halides, phosphates, acetates, lactates, alkyl sulfates, alkyl- or alkylaryl-sulfonates in which the alkyl and aryl groups preferably comprise, respectively, from 1 to 20 carbon atoms and from 6 to 30 carbon atoms. $R_{12}$ and $R_{13}$ preferably denote a mixture of alkenyl or alkyl groups containing from 12 to 21 carbon atoms, derived for example from tallow fatty acids, $R_{14}$ preferably denotes a methyl group, and $R_{15}$ preferably denotes a hydrogen atom. Such a product is sold, for example, under the name REWOQUAT W 75 by the company Rewo;

B. a quaternary diammonium or triammonium salt, in particular of formula (C):

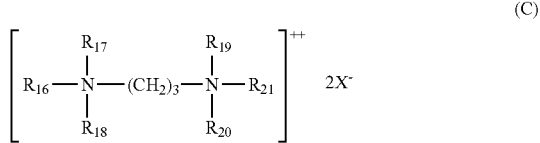
(C)

in which $R_{16}$ denotes an alkyl radical comprising approximately from 16 to 30 carbon atoms, which is optionally hydroxylated and/or interrupted with one or more oxygen atoms, $R_{17}$ is chosen from hydrogen or an alkyl radical comprising from 1 to 4 carbon atoms or a group $(R_{16a})(R_{17a})(R_{18a})N$—$(CH_2)_3$, $R_{16a}$, $R_{17a}$, $R_{18a}$, $R_{18}$, $R_{19}$, $R_{20}$ and $R_{21}$, which may be identical or different, being chosen from hydrogen and an alkyl radical comprising from 1 to 4 carbon atoms, and $X^-$ is an anion chosen from the group of halides, acetates, phosphates, nitrates and methyl sulfates. Such compounds are, for example, FINQUAT CT-P, sold by the company FINETEX (Quaternium 89), and FINQUAT CT, sold by the company FFINETEX (Quaternium 75), C. a quaternary ammonium salt containing at least one ester function, such as those of formula (D) below:

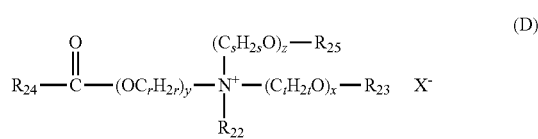
(D)

in which:

$R_{22}$ is chosen from $C_1$-$C_6$ alkyl groups and $C_1$-$C_6$ hydroxyalkyl or dihydroxyalkyl groups;

$R_{23}$ is chosen from:

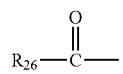

$R_{27}$, which is a linear or branched, saturated or unsaturated $C_1$-$C_{22}$ hydrocarbon-based group, and a hydrogen atom, $R_{25}$ is chosen from:

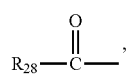

$R_{29}$, which is a linear or branched, saturated or unsaturated $C_1$-$C_6$ hydrocarbon-based group, and a hydrogen atom, R24, R26 and R28, which may be identical or different, are chosen from linear or branched, saturated or unsaturated C7-C21 hydrocarbon-based groups;

r, s and t, which may be identical or different, are integers ranging from 2 to 6;

y is an integer ranging from 1 to 10;

x and z, which may be identical or different, are integers ranging from 0 to 10;

X– is a simple or complex, organic or mineral anion;

with the proviso that the sum x+y+z is from 1 to 15, that when x is 0 then Rn denotes R27, and that when z is 0 then R25 denotes R29.

The alkyl groups R22 may be linear or branched, and more particularly linear. In some cases, R22 denotes a methyl, ethyl, hydroxyethyl or dihydroxypropyl group, and more particularly a methyl or ethyl group. Advantageously, the sum x+y+z is from 1 to 10.

When R23 is a hydrocarbon-based group R27, it may be long and contain from 12 to 22 carbon atoms, or may be short and contain from 1 to 3 carbon atoms. When R25 is an R29 hydrocarbon-based group, it preferably contains 1 to 3 carbon atoms. Advantageously, R24, R26 and R28, which may be identical or different, are chosen from linear or branched, saturated or unsaturated C11-C21 hydrocarbon-based groups, and more particularly from linear or branched, saturated or unsaturated C11-C21 alkyl and alkenyl groups.

In some cases, x and z, which may be identical or different, have values of 0 or 1. Likewise, in some cases y is equal to 1. In some cases, r, s and t, which may be identical or different, are equal to 2 or 3, and even more particularly are equal to 2.

The anion X– is may be a halide (chloride, bromide or iodide) or an alkyl sulfate, more particularly methyl sulfate. However, use may be made of methanesulfonate, phosphate, nitrate, tosylate, an anion derived from an organic acid, such as acetate or lactate, or any other anion compatible with the ammonium containing an ester function.

The anion X– is even more particularly chloride or methyl sulfate.

Use is made more particularly, in the composition according to the invention, of the ammonium salts of formula (D) in which:

R22 denotes a methyl or ethyl group, x and y are equal to 1;

z is equal to 0 or 1;

r, s and t are equal to 2;

R23 is chosen from:

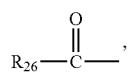

methyl, ethyl or $C_{14}$-$C_{22}$ hydrocarbon-based groups, and a hydrogen atom;

R25 is chosen from:

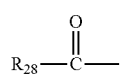

and a hydrogen atom;

R24, R26 and R28, which may be identical or different, are chosen from linear or branched, saturated or unsaturated C13-C17 hydrocarbon-based groups, and preferably from linear or branched, saturated or unsaturated C13-C17 alkyl and alkenyl groups. The hydrocarbon-based groups are advantageously linear.

Mention may be made, for example, of the compounds of formula (D) such as the diacyloxyethyldimethylammonium, diacylo xyethylhydroxyethylmethylammonium, monoacyloxyethyldihydroxyethylmethylammonium, triacyloxyethylmethylammonium and monoacyloxyethylhydroxyethyldimethylammonium salts (chloride or methyl sulfate in particular), and mixtures thereof. The acyl groups preferably contain 14 to 18 carbon atoms and are obtained more particularly from a plant oil, such as palm oil or sunflower oil. When the compound contains several acyl groups, these groups may be identical or different.

These products are obtained, for example, by direct esterification of triethanolamine, triisopropanolamine, an alkyldiethanolamine or an alkyldiisopropanolamine, which are optionally oxyalkylenated, with C10-C30 fatty acids or with mixtures of C10-C30 fatty acids of plant or animal origin, or by transesterification of the methyl esters thereof. This esterification is followed by quaternization using an alkylating agent such as an alkyl (preferably methyl or ethyl) halide, a dialkyl (preferably methyl or ethyl) sulfate, methyl methanesulfonate, methyl para-toluenesulfonate, glycol chlorohydrin or glycerol chlorohydrin. Such compounds are, for example, sold under the names DEHYQUART by the company Henkel, STEPANQUAT by the company Stepan, NOXAMIUM by the company Ceca or REWOQUAT WE 18 by the company Rewo-Witco.

The composition according to the invention may contain, for example, a mixture of quaternary ammonium monoester, diester and triester salts with a weight majority of diester salts.

Use may be made of behenoylhydroxypropyltrimethylammoniurn chloride.

Non-limiting examples of other cationic surfactants that can be used in the current compositions include dimethylamine derivatives, such as for example stearyl dimethyl amine, stearamidoproppyl dimethylamine, brassicamidopropyl dimethylamine, and mixtures thereof.

In an embodiment the cationic surfactant is selected from stearamidopropyl dimethylamine, commercially available under the tradename MACKINE 301, from Rhodia.

Cationic Polymers

The cationic polymers may be derived from polysaccharides, for example cationic cellulose derivatives, cationic starch derivatives, cationic guar derivatives and cationic locust bean gum derivatives, synthetic cationic polymers, mixtures or combinations of these agents. The compositions may comprise other synthetic or natural polymers or polymers derived from biological preparation processes, which are functionalized, where appropriate, for example with cationic or neutral groups. These polymers may have a stabilizing or strengthening action on the compositions, and/or a conditioning action (deposition on the surface of the skin or the hair).

Non-limiting examples of cationic polymers suitable for us in the compositions of the disclosure are polyquaternium compounds such as the diallyidimethylammonium chloride/acrylic acid copolymers sold under the names MERQUAT 280 POLYMER or MERQUAT 280NP POLYMER or MERQUAT 281 POLYMER or MERQUAT 295 POLYMER, by the company Nalco (Lubrizol) (INCI name: Polyquaternium-22); the copolymer of methacrylamidopropyltrimonium chloride, of acrylic acid and or methyl acrylate, sold under the name MERQUAT 2001 POLYMER OR MERQUAT 2001N POLYMER by the company Nalco (Lubrizol) (INCI name: Polyquaternium-47); the acrylamide/dimethyldiallylammonium chloride/acrylic acid terpolymer sold under the name MERQUAT 3330DRY POLYMER or MERQUAT 3330PR POLYMER or MERQUAT 3331PR POLYMER or MERQUAT 3940 POLYMER or MERQUAT PLUS 3330 POLYMER OR MERQUAT PLUS 3331 POLYMER by the company Nalco (Lubrizol) (INCI name: Polyquaternium-39); an ampholytic terpolymer consisting of methacrylamidopropyl trimethyl ammonium chloride (MAPTAC), acrylamide and acrylic acid, sold under the name MERQUAT 2003PR POLYMER by the company Nalco (Lubrizol) (INCI name: Polyquaternium-53); Polyquaternium-30, Polyquaternium-35, Polyquaternium-45, Polyquaternium-50, Polyquaternium-54; Polyquaternium-57; Polyquaternium-63; Polyquaternium-74; Polyquaternium-76; Polyquaternium-86; Polyquaternium-87 (polymeric quaternary ammonium salt of vinylpyrrolidone, N-Vinyl Imidazole, and diallyldimethyl ammonium chloride sold under the name LUVIQUAT Sensation by the company BASF); Polyquaternium-89; Polyquaternium-95; Polyquaternium-98, Polyquaternium-104; Polyquaternium-111; Polyquaternium-112, and mixtures thereof.

The compositions of the disclosure preferably contain the cationic agent in an amount of from about 0.05% to about 10% by weight, such as from about 0.1% to about 8% by weight, from about 0.2% to about 7% by weight, from about 0.25% to about 6% by weight, or from about 0.3% to about 5% by weight of active material, based on the total weight of the compositions.

Surfactants

The various compositions described herein may include one or more surfactants, including anionic, non-ionic and/or amphoteric/zwitterionic surfactants. Non-limiting examples of surfactants that may be used are provided below.

Nonionic Surfactants

Examples of nonionic surfactants that may be used are fatty alcohols, alpha-diols and (C1-C24)alkylphenols, these compounds being alkoxylated, polyethoxylated, polypropoxylated and/or polyglycerolated, and containing at least one fatty chain comprising, for example, from 8 to 18 carbon atoms, it being possible for the number of ethylene oxide and/or propylene oxide groups to especially range from 2 to 50, and for the number of glycerol groups to especially range from 2 to 30.

Mention may also be made of copolymers of ethylene oxide and propylene oxide, optionally oxyethylenated sorbitan fatty acid esters, sucrose fatty acid esters, polyoxyalkylenated fatty acid esters, polyoxyalkylenated fatty amides, optionally oxyalkylenated alkyl(poly)glucosides, alkylglucoside esters, derivatives of N-alkylglucamine and of N-acylmethylglucamine, aldobionamides, amine oxides and (poly)oxyalkylenated silicones.

Suitable examples are oleth-10, oleth-20, laureth-12, steareth-20, and mixtures thereof.

Other examples of nonionic surfactants that may be used are fatty alcohols such as stearyl alcohol, isostearyl alcohol, cetearyl alcohol, cetyl alcohol, lauryl alcohol, decyl alcohol, and mixtures thereof.

The nonionic surfactants can also be chosen from monooxyalkylenated or polyoxyalkylenated and monoglycerolated or polyglycerolated nonionic surfactants, and alkyl (poly)glucosides. The oxyalkylene units are more particularly oxyethylene or oxypropylene units, or a combination thereof, preferably oxyethylene units.

Useful nonionic surfactants may include: oxyalkylenated (C8-C24)alkylphenols; saturated or unsaturated, linear or branched, oxyalkylenated C8-C40 alcohols; saturated or unsaturated, linear or branched, oxyalkylenated C8-C30 amides; esters of saturated or unsaturated, linear or branched, C8-C30 acids and of polyethylene glycols; saturated or unsaturated, oxyethylenated plant oils; condensates of ethylene oxide and/or of propylene oxide, alone or as mixtures; oxyethylenated and/or oxypropylenated silicones; and alkyl(poly)glucosides.

As examples of monoglycerolated or polyglycerolated nonionic surfactants, monoglycerolated or polyglycerolated C8-C40 alcohols are useable. In particular, the monoglycerolated or polyglycerolated C C8-C40 alcohols correspond to formula (A1) below:

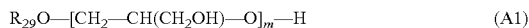

$$R_{29}O\text{—}[CH_2\text{—}CH(CH_2OH)\text{—}O]_m\text{—}H \tag{A1}$$

in which formula (A1):

$R_{29}$ represents a linear or branched $C_8$-$C_{40}$ and preferably $C_8$-$C_{30}$ alkyl or alkenyl radical; and m represents a number ranging from 1 to 30, or from 1 to 10.

As examples of compounds of formula (A1), mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol of formula (A1) may represent a mixture of alcohols in the same way that the value of m represents a statistical value, which means that, in a commercial product, several species of polyglycerolated fatty alcohols may coexist in the form of a mixture.

The alkyl(poly)glycoside nonionic surfactant(s) may be represented by formula (A2) below:

$$R_{30}O\text{—}(R_{31}O)_t(G)_v \tag{A2}$$

in which:

$R_{30}$ represents a saturated or unsaturated, linear or branched alkyl group comprising from about 8 to 24 carbon atoms, or an alkylphenyl group in which the linear or branched alkyl group comprises from 8 to 24 carbon atoms;

$R_{31}$ represents an alkylene group containing from about 2 to 4 carbon atoms, G represents a saccharide unit comprising from 5 to 6 carbon atoms, t denotes a value ranging from 0 to 10, or from 0 to 4, and v denotes a value ranging from 1 to 15.

In some cases, the alkyl(poly)glycoside nonionic surfactant(s) correspond to formula (IX) in which:

$R_{30}$ denotes a linear or branched, saturated or unsaturated alkyl group containing from 8 to 18 carbon atoms, G denotes glucose, fructose or galactose, preferably glucose, t denotes a value ranging from 0 to 3, and is preferably equal to 0, and $R_{31}$ and v are as defined previously.

The degree of polymerization of the alkyl(poly)glucoside nonionic surfactant(s), as represented, for example, by the index v in formula (IX), ranges on average from 1 to 15, or from 1 to 4. This degree of polymerization more particularly ranges from 1 to 2 and better still from 1.1 to 1.5, on average.

The glycoside bonds between the saccharide units are of 1.6 or 1.4 type and preferably of 1.4 type.

Examples of compounds of formula (A2) that may especially be mentioned are decyl glucoside, coco-glucoside, lauryl glucoside, such as the products sold by the company Cognis under the names PLANTAREN (600 CS/U, 1200 and 2000) or PLANTACARE (818, 1200 and 2000). Use may also be made of the products sold by the company SEPPIC under the names TRITON CG 110 (or ORAMIX CG 110) and Triton CG 312 (or ORAMIX NS 10), the products sold by the company BASF under the name LUTENSOL GD 70 or the products sold by the company Chem Y under the name AG10 LK. Use may also be made, for example, of the 1,4-(C8-C16)alkylpolyglucoside as an aqueous solution at 53% by weight relative to the total weight of the solution, sold by Cognis under the reference PLANTACARE 818 UP.

Amphoteric or Zwitterionic Surfactants

The amphoteric or zwitterionic surfactant that may be used in compositions according to the disclosure may be derivatives of aliphatic secondary or tertiary amines, optionally quaternized, in which derivatives the aliphatic group is a linear or branched chain comprising from 8 to 22 carbon atoms, the amine derivatives containing at least one anionic group, such as a carboxylate, sulfonate, sulfate, phosphate or phosphonate group. Mention may be made in particular of (C8-C20)alkylbetaines such as cocoylbetaine, sulfobetaines, (C8-C20)alkylamido(C2-C8)alkylbetaines such as cocoylamidopropylbetaine or (C8-C20)alkylamido(C6-C8)-alkylsulfobetaines, and mixtures thereof.

Among the derivatives of aliphatic secondary or tertiary amines, optionally quaternized, that may be used, as defined above, mention may also be made of the compounds of respective structures (I), (II) and (IIa) below:

$$Ra\text{—}C(O)\text{—}NHCH_2CH_2\text{—}N^+(Rb)(Rc)\text{—}CH_2COO^-, M^+, X^- \tag{I}$$

in which formula (I):

Ra represents a C10-C30 alkyl or alkenyl group derived from an acid Ra—COOH preferably present in hydrolysed coconut oil, or a heptyl, nonyl or undecyl group;

Rb represents a beta-hydroxyethyl group; and

Rc represents a carboxymethyl group;

M+ represents a cationic counterion derived from an alkali metal or alkaline-earth metal, such as sodium, an ammonium ion or an ion derived from an organic amine; and X– represents an organic or mineral anionic counterion, such as that chosen from halides, acetates, phosphates, nitrates, (C1-C4)alkyl sulfates, (C1-C4)alkyl- or (C1-C4)alkylarylsulfonates, in particular methyl sulfate and ethyl sulfate; or alternatively M+ and X– are absent;

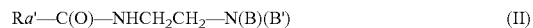

$$Ra'\text{—}C(O)\text{—}NHCH_2CH_2\text{—}N(B)(B') \tag{II}$$

in which formula (II):

B represents the group —CH2-CH2-O—X';

B' represents the group —(CH2)zY', with z=1 or 2;

X' represents the group —CH2-COOH, CH2-COOZ', —CH2CH2-COOH or —CH2CH2-COOZ', or a hydrogen atom;

Y' represents the group —COOH, —COOZ', CH2CH(OH)SO3H or the group —CH2CH(OH)SO3Z';

Z' represents a cationic counterion derived from an alkali metal or alkaline-earth metal, such as sodium, an ammonium ion or an ion derived from an organic amine;

Ra' represents a C10-C30 alkyl or alkenyl group of an acid Ra'—COOH, which may be coconut oil or in hydrolysed linseed oil, or an alkyl group, especially a C17 group and its iso form, or an unsaturated C17 group.

The compounds of this type are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid and cocoamphodipropionic acid.

By way of example, mention may be made of the cocoamphodiacetate sold by the company Rhodia under the trade name Miranol C2M Concentrate and the cocoamphodipropionate sold by the company Evonik Goldschmidt under the trade name Rewoteric AM KSF 40.

$$Ra''\text{—}NH\text{—}CH(Y'')\text{—}(CH_2)_n\text{—}C(O)\text{—}NH\text{—}(CH_2)_{n'}\text{—}N(Rd)(Re) \quad (IIa)$$

in which formula (IIa):

Y″ represents the group —COOH, —COOZ″, —CH2CH(OH)SO3H or the group —CH2CH(OH)SO3Z″;

Rd and Re, independently of each other, represent a C1-C4 alkyl or hydroxyalkyl radical;

Z″ represents a cationic counterion derived from an alkali metal or alkaline-earth metal, such as sodium, an ammonium ion or an ion derived from an organic amine;

Ra″ represents a C10-C30 alkyl or alkenyl group of an acid Ra″—COOH;

n and n′ denote, independently of each other, an integer ranging from 1 to 3; and mixtures of these compounds.

Among the compounds of formula (IIa), mention may be made of the compound classified in the CTFA dictionary under the name sodium diethylaminopropyl cocoaspartamide and sold by the company Chimex under the name Chimexane HB. In some instances, the amphoteric or zwitterionic surfactant(s) are chosen from cocoylbetaine, cocoylamidopropylbetaine and sodium cocoylamidoethyl-N-hydro xyethylaminopropionate.

Anionic Surfactants

The term "anionic surfactant" means a surfactant comprising, as ionic or ionizable groups, only anionic groups. These anionic groups are chosen preferably from the groups CO2H, CO2-, SO3H, SO3-, OSO3H, OSO3-O2PO2H, O2PO2H and O2PO22-.

The anionic surfactant(s) that may be used may be alkyl sulfates, alkyl ether sulfates, alkylamido ether sulfates, alkylaryl polyether sulfates, monoglyceride sulfates, alkylsulfonates, alkylamide sulfonates, alkylarylsulfonates, alpha-olefin sulfonates, paraffin sulfonates, alkylsulfosuccinates, alkyl ether sulfosuccinates, alkylamide sulfosuccinates, alkyl sulfoacetates, acylsarcosinates, acylglutamates, alkylsulfosuccinamates, acyl isethionates and N-acyltaurates, salts of alkyl monoesters and polyglycoside-polycarboxylic acids, acyllactylates, salts of D-galactoside uronic acids, salts of alkyl ether carboxylic acids, salts of alkyl aryl ether carboxylic acids, and salts of alkylamido ether carboxylic acids; or the non-salified forms of all of these compounds, the alkyl and acyl groups of all of these compounds containing from 6 to 24 carbon atoms and the aryl group denoting a phenyl group. Some of these compounds may be oxyethylenated and then preferably comprise from 1 to 50 ethylene oxide units.

The salts of C6-C24 alkyl monoesters of polyglycoside-polycarboxylic acids may be chosen from C6-C24 alkyl polyglycoside-citrates, C6-C24 alkyl polyglycoside-tartrates and C6-C24 alkyl polyglycoside-sulfo succinates.

When the anionic surfactant(s) are in salt form, they may be chosen especially from alkali metal salts such as the sodium or potassium salt and preferably the sodium salt, ammonium salts, amine salts and in particular amino alcohol salts, or alkaline-earth metal salts such as the magnesium salt.

Examples of amino alcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts. Alkali metal or alkaline-earth metal salts and in particular the sodium or magnesium salts may be used.

Use is also made of (C6-C24)alkyl sulfates, (C6-C24) alkyl ether sulfates, which are optionally ethoxylated, comprising from 2 to 50 ethylene oxide units, and mixtures thereof, in particular in the form of alkali metal salts or alkaline-earth metal salts, ammonium salts or amino alcohol salts. More preferentially, the anionic surfactant(s) are chosen from (C10-C20)alkyl ether sulfates, and in particular sodium lauryl ether sulfate containing 2.2 mol of ethylene oxide.

The compositions of the disclosure preferably contain the cationic agent in an amount of from about 0.05% to about 20% by weight, such as from about 0.1% to about 15% by weight, from about 0.2% to about 12% by weight, from about 0.25% to about 10% by weight, or from about 0.3% to about 8% by weight of active material, based on the total weight of the compositions.

Silicones

The compositions of the present disclosure may further comprise one or more silicone compounds other than the silane compound (b). The one or more silicone compounds may be chosen from amino silicones and non-amino silicones (no amino groups) such as dimethicone, and mixtures thereof.

In an embodiment, the one or more silicone compounds of the present disclosure is an amino silicone.

The term "amino silicone" is intended to mean any silicone comprising at least one primary, secondary or tertiary amine or a quaternary ammonium group (i.e., a quaternized group).

As amino silicone that may be used in the scope of the instant disclosure, the following can be cited:

a) polysiloxanes corresponding to formula (A):

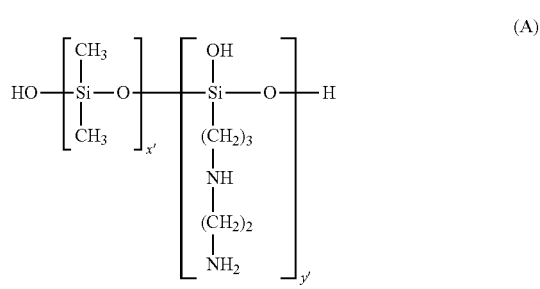

in which x′ and y′ are integers such that the weight-average molecular weight (Mw) is comprised between about 5000 and 500 000;

b) amino silicones corresponding to formula (B):

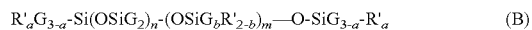

$$R'_aG_{3-a}\text{-Si}(OSiG_2)_n\text{-}(OSiG_bR'_{2-b})_m\text{—O-SiG}_{3-a}\text{-}R'_a \quad (B)$$

in which:

G, which may be identical or different, designate a hydrogen atom, or a phenyl, OH or $C_1$-$C_8$ alkyl group, for example methyl, or $C_1$-$C_8$ alkoxy, for example methoxy, a, which may be identical or different, denote the number 0 or an integer from 1 to 3, in particular 0;

b denotes 0 or 1, and in particular 1;

m and n are numbers such that the sum (n+m) ranges from 1 to 2000 and in particular from 50 to 150, it being possible for n to denote a number from 0 to 1999 and in particular from 49 to 149, and for m to denote a number from 1 to 2000 and in particular from 1 to 10;

R', which may be identical or different, denote a monovalent radical having formula —$C_qH_{2q}L$ in which q is a number ranging from 2 to 8 and L is an optionally quaternized amino group chosen from the following groups:

—NR"-Q-N(R")$_2$

—N(R")$_2$

—N+(R")$_3$A-

—N+H(R")$_2$A-

—N+H$_2$(R")A-

—N(R")-Q-N+R"H$_2$A-

—NR"-Q-N+(R")$_2$HA-

—NR"-Q-N+(R")$_3$A-, in which R", which may be identical or different, denote hydrogen, phenyl, benzyl, or a saturated monovalent hydrocarbon-based radical, for example a $C_1$-$C_{20}$ alkyl radical; Q denotes a linear or branched $C_rH_{2r}$ group, r being an integer ranging from 2 to 6, preferably from 2 to 4; and A– represents a cosmetically acceptable ion, in particular a halide such as fluoride, chloride, bromide or iodide.

A group of amino silicones corresponding to this definition (B) is represented by the silicones called "trimethylsilylamodimethicone" having formula (C):

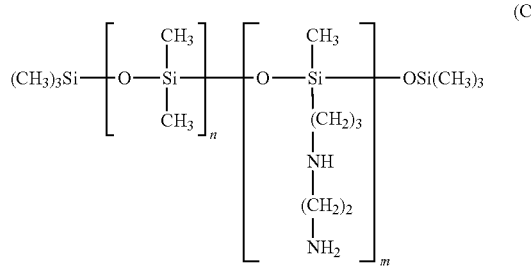

(C)

in which n and m have the meanings given above, in formula B.

Another group of amino silicones corresponding to this definition is represented by silicones having the following formulae (D) or (E):

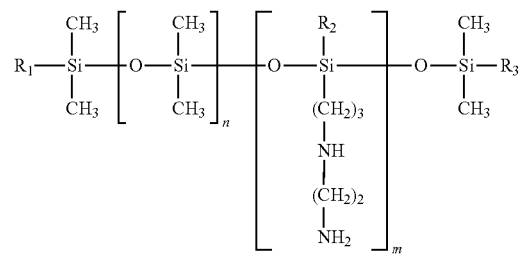

(D)

in which:

m and n are numbers such that the sum (n+m) can range from 1 to 1000, in particular from 50 to 250 and more particularly from 100 to 200, it being possible for n to denote a number from 0 to 999 and in particular from 49 to 249, and more particularly from 125 to 175, and for m to denote a number from 1 to 1000 and in particular from 1 to 10, and more particularly from 1 to 5;

$R_1$, $R_2$, $R_3$, which may be identical or different, represent a hydroxy or $C_1$-$C_4$ alkoxy radical, where at least one of the radicals $R_1$ to $R_3$ denotes an alkoxy radical.

The alkoxy radical is preferably a methoxy radical.

The hydroxy/alkoxy mole ratio ranges preferably from 0.2:1 to 0.4:1 and preferably from 0.25:1 to 0.35:1 and more particularly equals 0.3:1.

The weight-average molecular weight (Mw) of the silicone ranges preferably from 2000 to 1 000 000, more particularly from 3500 to 200 000.

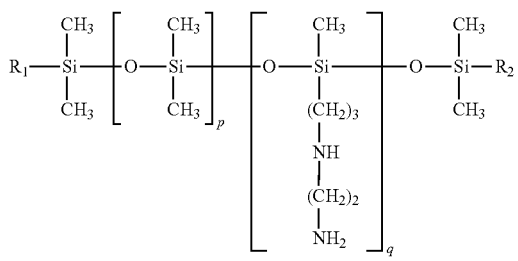

(E)

in which:

p and q are numbers such that the sum (p+q) ranges from 1 to 1000, particularly from 50 to 350, and more particularly from 150 to 250; it being possible for p to denote a number from 0 to 999 and in particular from 49 to 349, and more particularly from 159 to 239 and for q to denote a number from 1 to 1000, in particular from 1 to 10, and more particularly from 1 to 5;

$R_1$, $R_2$, which are different, represent a hydroxy or $C_1$-$C_4$ alkoxy radical, where at least one of the radicals $R_1$ or $R_2$ denotes an alkoxy radical.

The alkoxy radical is preferably a methoxy radical.

The hydroxy/alkoxy mole ratio ranges generally from 1:0.8 to 1:1.1 and preferably from 1:0.9 to 1:1 and more particularly equals 1:0.95.

The weight-average molecular weight (Mw) of the silicone ranges preferably from 2000 to 200 000, even more particularly 5000 to 100 000 and more particularly from 10 000 to 50 000.

Commercial products corresponding to these silicones having structure (D) or (E) may include in their composition one or more other amino silicones whose structure is different than formulae (D) or (E).

A product containing amino silicones having structure (D) is sold by Wacker under the name Belsil® ADM 652.

A product containing amino silicones having structure (E) is sold by Wacker under the name Fluid WR 1300®.

When these amino silicones are used, one particularly advantageous embodiment consists in using them in the form of an oil-in-water emulsion. The oil-in-water emulsion may comprise one or more surfactants. The surfactants may be of any nature but are preferably cationic and/or nonionic. The number-average size of the silicone particles in the emulsion generally ranges from 3 nm to 500 nanometers. Preferably, in particular as amino silicones having formula (E), microemulsions are used whose average particle size ranges from 5 nm to 60 nanometers (limits included) and more preferably from 10 nm to 50 nanometers (limits included). Accordingly, according to the invention the microemulsions of amino silicone having formula (E) sold as Finish CT 96 E® or SLM 28020® by Wacker can be used.

Another group of amino silicones corresponding to this definition is represented by the following formula (F):

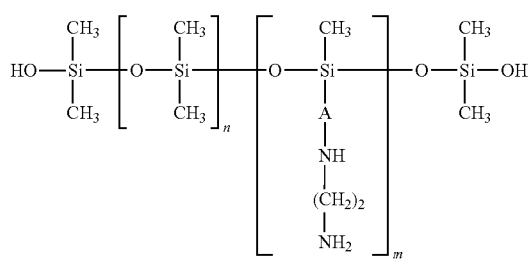

(F)

in which:
m and n are numbers such that the sum (n+m) ranges from 1 to 2000 and in particular from 50 to 150, it being possible for n to denote a number from 0 to 1999 and in particular from 49 to 149, and for m to denote a number from 1 to 2000 and in particular from 1 to 10;

A denotes a linear or branched alkylene radical containing from 4 to 8 carbon atoms and preferably 4 carbon atoms. This radical is preferably linear.

The weight-average molecular weight (Mw) of these amino silicones ranges preferably from 2000 to 1 000 000 and even more particularly from 3500 to 200 000.

A preferred silicone of formula (F) is amodimethicone (INCI name) sold under the tradename XIAMETER® MEM-8299 Cationic Emulsion by Dow Corning.

Another group of amino silicones corresponding to this definition is represented by the following formula (G):

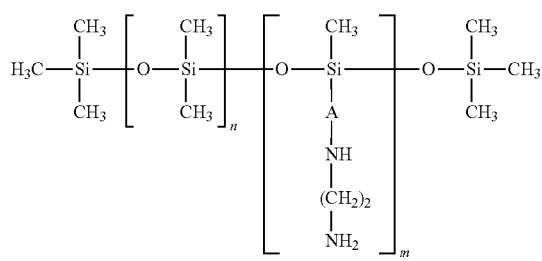

(G)

in which:
m and n are numbers such that the sum (n+m) ranges from 1 to 2000 and in particular from 50 to 150, it being possible for n to denote a number from 0 to 1999 and in particular from 49 to 149, and for m to denote a number from 1 to 2000 and in particular from 1 to 10;

A denotes a linear or branched alkylene radical containing from 4 to 8 carbon atoms and preferably 4 carbon atoms. This radical is preferably branched.

The weight-average molecular weight (Mw) of these amino silicones ranges preferably from 500 to 1 000 000 and even more particularly from 1000 to 200 000.

A silicone having this formula is for example DC2-8566 Amino Fluid by Dow Corning.

c) amino silicones corresponding to formula (H):

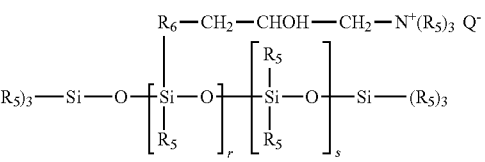

(H)

in which:
$R_5$ represents a monovalent hydrocarbon-based radical containing from 1 to 18 carbon atoms, and in particular a $C_1$-$C_{18}$ alkyl or $C_2$-$C_{18}$ alkenyl radical, for example methyl;

$R_6$ represents a divalent hydrocarbon-based radical, in particular a $C_1$-$C_{18}$ alkylene radical or a divalent $C_1$-$C_{18}$, for example $C_1$-$C_8$, alkylenoxy radical linked to the Si via an SiC bond;

Q- is an anion such as a halide ion, in particular chloride, or an organic acid salt (for example acetate);

r represents a mean statistical value from 2 to 20 and in particular from 2 to 8;

s represents a mean statistical value from 20 to 200 and in particular from 20 to 50.

Such amino silicones are described more particularly in U.S. Pat. No. 4,185,087.

d) quaternary ammonium silicones having formula (I):

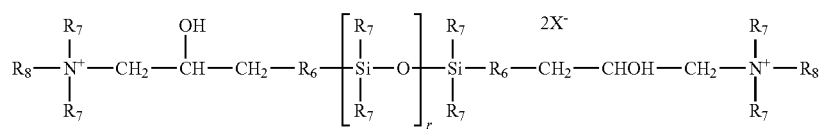

(I)

in which:

R_7, which may be identical or different, represent a monovalent hydrocarbon-based radical containing from 1 to 18 carbon atoms, and in particular a $C_1$-$C_{18}$ alkyl radical, a $C_2$-$C_{18}$ alkenyl radical or a ring containing 5 or 6 carbon atoms, for example methyl;

$R_6$ represents a divalent hydrocarbon-based radical, in particular a $C_1$-$C_{18}$ alkylene radical or a divalent $C_1$-$C_{18}$, for example $C_1$-$C_8$, alkylenoxy radical linked to the Si via an SiC bond;

$R_8$, which may be identical or different, represent a hydrogen atom, a monovalent hydrocarbon-based radical containing from 1 to 18 carbon atoms, and in particular a $C_1$-$C_{18}$ alkyl radical, a $C_2$-$C_{18}$ alkenyl radical or a —$R_6$—NHCOR_7 radical;

X— is an anion such as a halide ion, in particular chloride, or an organic acid salt (for example acetate);

r represents a mean statistical value from 2 to 200 and in particular from 5 to 100;

These silicones are described, for example, in patent application EP-A 0 530 974.

e) amino silicones having formula (J):

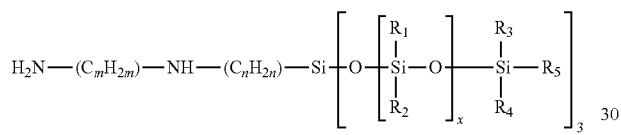

(J)

in which:

$R_1$, $R_2$, $R_3$ and $R_4$, which may be identical or different, denote a $C_1$-$C_4$ alkyl radical or a phenyl group;

$R_5$ denotes a $C_1$-$C_4$ alkyl radical or a hydroxyl group;

n is an integer ranging from 1 to 5;

m is an integer ranging from 1 to 5;

and in which x is chosen such that the amine number is between 0.01 and 1 meq/g;

f) multiblockpolyoxyalkylenated amino silicones, of type (AB)n, A being a polysiloxane block and B being a polyoxyalkylenated block containing at least one amine group.

Said silicones are preferably constituted of repeating units having the following general formulae:

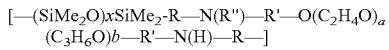

or alternatively

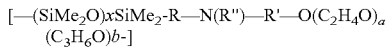

in which:

a is an integer greater than or equal to 1, preferably ranging from 5 to 200, more particularly ranging from 10 to 100;

b is an integer comprised between 0 and 200, preferably ranging from 4 to 100, more particularly between from 5 and 30;

x is an integer ranging from 1 to 10 000, more particularly from 10 to 5000;

R" is a hydrogen atom or a methyl;

R, which may be identical or different, represent a divalent linear or branched $C_2$-$C_{12}$ hydrocarbon-based radical, optionally including one or more heteroatoms such as oxygen; preferably R denotes an ethylene radical, a linear or branched propylene radical, a linear or branched butylene radical, or a —$CH_2CH_2CH_2OCH(OH)CH_2$— radical; preferentially R denotes a —$CH_2CH_2CH_2OCH(OH)CH_2$— radical;

R', which may be identical or different, represent a divalent linear or branched $C_2$-$C_{12}$ hydrocarbon-based radical, optionally including one or more heteroatoms such as oxygen; preferably, R' denotes an ethylene radical, a linear or branched propylene radical, a linear or branched butylene radical, or a —$CH_2CH_2CH_2OCH(OH)CH_2$— radical; preferentially R' denotes —$CH(CH_3)$—$CH_2$—.

The siloxane blocks preferably represent between 50 and 95 mol % of the total weight of the silicone, more particularly from 70 to 85 mol %.

The amine content is preferably between 0.02 and 0.5 meq/g of copolymer in a 30% solution in dipropylene glycol, more particularly between 0.05 and 0.2.

The weight-average molecular weight (Mw) of the silicone is preferably comprised between 5000 and 1 000 000, more particularly between 10 000 and 200 000.

Mention may be made especially of the silicones sold under the names Silsoft™ A-843 or Silsoft™ A+ by Momentive.

g) the alkylamino silicones corresponding to formula (K) below:

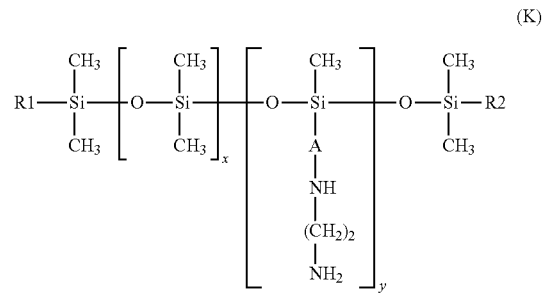

(K)

in which:

x and y are numbers ranging from 1 to 5000; preferably, x ranges from 10 to 2000 and especially from 100 to 1000; preferably, y ranges from 1 to 100;

$R_1$ and $R_2$, which may be identical or different, preferably identical, are linear or branched, saturated or unsaturated alkyl radicals, comprising 6 to 30 carbon atoms, preferably 8 to 24 carbon atoms and especially 12 to 20 carbon atoms;

A denotes a linear or branched alkylene radical containing from 2 to 8 carbon atoms, Preferably, A comprises 3 to 6 carbon atoms, especially 4 carbon atoms; preferably, A is branched. Mention may be made especially of the following divalent radicals: —$CH_2CH_2CH_2$— and —$CH_2CH(CH_3)CH_2$—.

Preferably, R1 and R2, which may be identical or different, are saturated linear alkyl radicals comprising 6 to 30 carbon atoms, preferably 8 to 24 carbon atoms and especially 12 to 20 carbon atoms; mention may be made in particular of dodecyl, tetradecyl, pentadecyl, hexadecyl, heptadecyl, octadecyl, nonadecyl and eicosyl radicals; and preferentially, R1 and R2, which may be identical or different, are chosen from hexadecyl (cetyl) and octadecyl (stearyl) radicals.

Preferentially, the silicone is of formula (K) with:

x ranging from 10 to 2000 and especially from 100 to 1000;

y ranging from 1 to 100;

A comprising 3 to 6 carbon atoms and especially 4 carbon atoms; preferably, A is branched; and more particularly A is chosen from the following divalent radicals: $CH_2CH_2CH_2$ and $—CH_2CH(CH_3)CH_2—$; and $R_1$ and $R_2$, which may be identical or different, being linear, saturated alkyl radicals comprising 6 to 30 carbon atoms, preferably 8 to 24 carbon atoms and especially 12 to 20 carbon atoms; chosen in particular from dodecyl, tetradecyl, pentadecyl, hexadecyl, heptadecyl, octadecyl, nonadecyl and eicosyl radicals; preferentially, $R_1$ and $R_2$, which may be identical or different, being chosen from hexadecyl (cetyl) and octadecyl (stearyl) radicals.

A preferred silicone of formula (K) is bis-cetearylamodimethicone (INCI name).

Mention may be made especially of the silicone sold under the name Silsoft™ AX by Momentive.

h) silicone compounds with at least one quaternary ammonium group. Suitable non-limiting examples are quaternium 80, silicone quaternium-1, silicone quaternium-2, silicone quaternium-2 panthenol succinate, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, silicone quaternium-16, silicone quaternium-16/Glycidoxy Dimethicone Crosspolymer, silicone quaternium-17, silicone quaternium-18, silicone quaternium-20 and silicone quaternium-21. Preferred are quaternium 80, silicone quaternium-16, silicone quaternium-18, silicone quaternium-1, silicone quaternium-2, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, silicone quaternium-17, silicone quaternium-20 and silicone quaternium-21. More preferred are quaternium 80, silicone quaternium-16, silicone quaternium-18, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, and silicone quaternium-17. Most preferred are quaternium 80, silicone quaternium-16, silicone quaternium-18, silicone quaternium-15, and mixtures thereof.

The silicone compounds with at least one quaternary ammonium group can also include those compounds of formula (B) when L in formula (B) is a quaternized amino group as described.

In an embodiment, the one or more silicone compounds of the present disclosure is a non amino silicone compound such as a dimethicone compound.

In an embodiment, the one or more silicone compounds of the present disclosure is an amino silicone compound such as amodimethicone.

The silicone compound of the present disclosure may be provided or may be commercially available in emulsion form that further comprises surfactants chosen from nonionic surfactants, cationic surfactants, and mixtures thereof. In certain embodiments, the emulsion in which the silicone compound is contained is a microemulsion.

The silicone compound(s) may be present in the composition according to the invention in an amount of about 0.05% to about 5% by weight, such as from about 0.1% to about 4% by weight, from about 0.15% to about 3% by weight, from about 0.2% to about 3% by weight, or from about 0.3% to about 2.5%, by weight of the active material, based on the total weight of the composition, including all ranges and subranges therebetween.

In some embodiments, the silicone compound(s) may be introduced into the compositions of the invention in the form of an emulsion material in an amount of about 0.05% to about 8% by weight, such as from about 0.1% to about 7% by weight, from about 0.15% to about 6% by weight, from about 0.2% to about 5% by weight, or from about 0.3% to about 4%, by weight of the active material, based on the total weight of the compositions, including all ranges and subranges therebetween.

In various embodiments, the total amount of silicone compound(s) is about 0.01%, 0.025%, 0.04%, 0.05%, 0.075%, 0.1%, 0.15%, 0.2%, 0.25%, 0.3%, 0.325%, 0.35%, 0.4%, 0.44%, 0.45%, 0.5%, 0.55%, 0.6%, 0.64%, 0.65%, 0.7%, 0.75%, 0.774%, 0.8%, 0.85%, 0.88%, 0.9%, 0.95%, 1%, 1.25%, 1.5%, 1.75%, 2%, 2.25% 2.5%, 2.75%, 3%, 3.25% 3.5%, 3.75%, or 4% by weight of the active material or the emulsion material, based on the total weight of the composition.

Conditioning Agents

The compositions may contain one or more conditioning agents such as esters, oils, emollients, and mixtures thereof.

Forms

The compositions described herein may be in any suitable physical form. Suitable forms include, but are not limited to low to moderate viscosity liquids, creams, lotions, milks, mousses, sprays, gels, and the like. Suitable excipients, such as those listed above, are included or excluded from the hair coloring formulation depending on the form of use of the formulation (e.g., spray, cream, gel, etc.).

i. Creams

The compositions disclosed herein for coloring hair may be in the form of a cream. The cream can be prepared as emulsions, for example, oil in water or water in oil or water in oil in water emulsions and will generally contain one or more of emulsifying agents, nonionic surfactants, anionic surfactants, cationic agents, conditioning agents, fatty alcohols, oils, and mixtures thereof.

ii. Gels

The compositions disclosed herein for coloring hair may be in the form of a gel. The gels will typically contain a cosmetically acceptable carrier such as water and will generally contain one or more of gelling agents, structuring agents, rheology or viscosity modifying agents, and mixtures thereof.

iii. Spray

The compositions described herein for coloring hair may be in the form of a spray. The spray typically includes the coloring composition in a cosmetically acceptable carrier. In some embodiments, the carrier is water or a water and alcohol mixture. The spray formulation optionally includes an emollient, thickener, hair conditioning agent, polymer, and/or surfactant. The hair spray formulations may be dispensed from containers that include aerosol dispensers or pump spray dispensers. Such dispensers are known in the art and are commercially available from a variety of manufacturers.

When the hair spray formulation is dispensed from a pressurized aerosol container, a propellant may be used to force the composition out of the container. Suitable propellants include, but are not limited to, a liquefiable gas or a halogenated propellant. Examples of suitable propellants include dimethyl ether and hydrocarbon propellants such as propane, n-butane, iso-butane, CFCs, and CFC-replacement propellants. The propellants may be used singly or admixed.

The amount of propellant may range from about 10% to about 60% by weight of the formulation. The propellant may be separated from the hair color formulation as in a two compartment container. Other suitable aerosol dispensers are those characterized by the propellant being compressed air, which can be filled into the dispenser using a pump or equivalent device prior to use. Conventional non-aerosol pump spray dispensers, i.e., atomizers, may also be used to apply the hair strengthening formulation to the hair.

Kits, and Methods

Other aspects of the invention pertain to kits comprising various combinations of the pre-color treatment, post-color treatment, coloring and developer compositions described herein. For example, The developer may be present in a separate container from the coloring composition. The coloring composition may, in some embodiments, be ready for mixing with the developer. In such embodiments, the developer and hair coloring composition are combined just prior to use.

In other embodiments, each of the above-described components (pre-colors treatment comprising the metal salts, coloring composition, post-color treatment, and developer) are packaged in separate containers.

In an embodiment, the one or more divalent metal salts of an inorganic acid (a), the one or more monovalent or divalent metal salts of an organic acid (b), the hair coloring composition containing one or more colorants chosen from oxidative dye precursors, direct dyes, pigments, and mixtures thereof, and post-color treatment composition can be packaged in separate containers.

In an embodiment, the metal salts (a) and (b) are packaged together in one container as a pre-color treatment composition, and the coloring composition and the post-color treatment composition can be packaged in separate containers.

In yet another embodiment, each of the metal salts (a) and (b) are provided as separate compositions and packaged in different containers.

The pre-treatment composition or each of the metal salt components, (a) and (b), can be in liquid form (for example, aqueous form in water or emulsion/lotion form or serum).

Another aspect of the invention pertains to methods of using the pre-color treatment and post-color treatment compositions. The methods comprise applying the pre-color treatment compositions or metal salt components in a sequential manner described herein to human hair. The pre-color treatment composition may be left on the hair for a period of time for up to one hour, such as from about 30 second to about 45 minutes, from about 1 minute to about 30 minutes, or from about 5 minutes to about 20 minutes. In further embodiments, the dye composition may be left on the hair for a period up to about 30 minutes, such as, for example, from about 1 to about 30 minutes, about 1 to about 10 minutes, or about 1 to about 5 minutes, or about 10 seconds to about 1 minute.

The methods of the present disclosure may involve dyeing the hair by use of the coloring compositions described herein and dye compositions resulting from the combination of the coloring composition and oxidizing composition (developer). The methods comprise applying the dyes compositions described herein to human hair. The dye composition may be left on the hair for a period of time sufficient to achieve the desired alteration in hair tone. For example, the dye composition may be left on the hair for up to one hour, such as from about 3 minutes to about 45 minutes, from about 5 minutes to about 30 minutes, or from about 10 minutes to about 20 minutes. In further embodiments, the dye composition may be left on the hair for a period up to about 30 minutes, such as, for example, from about 1 to about 30 minutes, about 1 to about 10 minutes, or about 1 to about 5 minutes. One skilled in the art will, by considering various factors such as the starting and desired tones of the hair, be able to determine an appropriate amount of time to leave the dye composition on the hair in order to achieve the desired alteration in hair tone. By way of non-limiting example, various embodiments according to the disclosure may provide for an increase of 1 to 4 in the tone height of the hair.

In some embodiments, the dye composition may, optionally, be shampooed and/or rinsed off the hair.

In preferred embodiments, the dye composition is shampooed and/or rinsed off the hair.

Thus, another aspect of the invention pertains to a method for preventing or minimizing the fading of the artificial color or hair during washing or shampooing, the method comprising contacting hair with a post-color treatment composition for a sufficient period of time, and wherein the post-color treatment composition comprises from about 1 wt. % to about 30 wt. % of one or more silane compounds corresponding to formula (Ia):

$$R_1Si(OR_2)_z(R_3)_x(OH)_y \tag{Ia}$$

in which:

R1 is a cyclic or acyclic, linear or branched, saturated or unsaturated C1-C22, in particular C2-C20, hydrocarbon-based chain, which may be substituted with a group chosen from amine groups NH2 or NHR (R being a linear or branched C1-C20, in particular C1-C6, alkyl, a C3-C40 cycloalkyl or a C6-C30 aromatic radical); the hydroxyl group (OH), a thiol group, an aryl group (more particularly benzyl), which is possibly substituted with an NH2 or NHR group; it being possible for R1 to be interrupted with a heteroatom (O, S or NH) or a carbonyl group (CO), R2 and R3, which may be identical or different, represent a linear or branched alkyl group comprising from 1 to 6 carbon atoms, y denotes an integer ranging from 0 to 3, and z denotes an integer ranging from 0 to 3, and x denotes an integer ranging from 0 to 2, with z+x+y=3.

In an embodiment, the method of the present disclosure comprises contacting hair with the pre-color treatment composition in order to impart anti-fading properties to hair, followed by artificially coloring the hair, and then followed by contacting the hair with the post-color treatment composition in order to boost the anti-fading properties of the artificial color of hair.

In various embodiments, the post-color treatment composition is applied onto the artificially colored hair at various times such as after drying the hair after the initial coloration, or on subsequent days before the next coloration, such as prior to washing or shampooing the hair. The post-color treatment composition can be applied to the hair before every washing or shampooing or whenever desired.

The post-color treatment composition may be left on the hair for a period of time for up to one hour, such as from about 30 second to about 45 minutes, from about 1 minute to about 30 minutes, or from about 5 minutes to about 20 minutes. In further embodiments, the dye composition may be left on the hair for a period up to about 30 minutes, such as, for example, from about 1 to about 30 minutes, about 1 to about 25 minutes, or about 1 to about 20 minutes.

Implementation of the present disclosure is provided by way of the following examples. The examples serve to illustrate the technology without being limiting in nature.

EXAMPLES

Example 1

Assessing the Efficacy of a Pre-Color Treatment Containing Zinc Gluconate and Calcium Chloride for Hair Color Protection Against Shampooing.

Normal bleached hair swatches (from IHIP, about 1.5 grams) were treated and evaluated as set forth below.

Pre-Color Treatment:

Normal bleached hair swatches were treated with a pre-color treatment of a 10 wt. % zinc gluconate solution or a 30 wt. % calcium chloride solution or a 10 wt. % zinc gluconate and a 30% wt. % calcium chloride solution (0.5 g solution/1 g of hair). The treated hair swatches were allowed to stand at room temperature for 20 minutes then blow dried.

Color Treatment:

The treated hair swatches and untreated hair swatches (control) were colored using a hair coloring product (1 g color cream/1.5 g developer/1 g hair) for a period of time (30 minutes) to give the hair a desired color (intense auburn). The hair coloring product is a dye mixture containing a color cream composition and a developer composition. The color cream composition contained oxidative dyes and the developer contained an oxidizing agent (hydrogen peroxide). The developer composition can contain different amounts of the oxidizing agent depending on the desired lift or lightening of the color on the hair.

Hair Shampooing:

The colored/treated and untreated hair swatches were washed with an anionic shampoo (containing 12 wt. % sodium laureth sulfate, pH=5.5) 10 times (one shampoo treatment is one wash cycle). The hair swatches were rinsed with water and blown dry after each shampoo.

Color Assessment:

For determining the degree of change in the color of hair (e.g. degree of lightening of the color or color deposit), measurements of L*, a*, and b* values of the hair swatches were obtained before and after 10 shampoos. The L*a*b* colorimetric system is a colorimetric system that assigns each color to a position in a spherical color space. In this color space, the brightness is represented by a position in the ordinate (z-axis) direction, the hue is represented by a position in the circumferential direction, and the chroma is represented by a distance from the center axis. The position on the ordinate (z-axis) representing brightness is designated by L*, and the L* value changes from 0 corresponding to black to 100 corresponding to white. The positive direction of the x-axis corresponds to a red direction, the positive direction of the y-axis corresponds to a yellow direction, the negative direction of the x-axis corresponds to a green direction, the negative direction of the y-axis corresponds to a blue direction, and the position on the x-axis is designated by a* of which value changes from −60 to +60 and the position on the y-axis is designated by b* of which value changes from −60 to +60. The hue and chroma are represented by a* value and b* value, respectively. The higher the L*, the lighter the color of the hair; the higher the a*, the more the hue shifts to red (i.e., the hair is redder); and the lower the b*, the more the chroma value shifts to blue. Delta-E (LE) which is calculated from the L*, a*, and b* values represents the overall color change on the swatches (from control or baseline).

The results of the treatments described above are provided below in table 1.

TABLE 1

| Treatment | Delta-E (ΔE) | |
|---|---|---|
| | 6 shampoos | 10 shampoos |
| No Treatment (control)* | 3.4 | 6.8 |
| Pre-color treatment with 10 wt. % zinc gluconate solution | 4.3 | 5.6 |
| Pre-color treatment with 30 wt. % calcium chloride solution | 8.3 | 10.5 |
| Pre-color treatment with 10 wt. % zinc gluconate and a 30 wt. % calcium chloride solution (invention) | 2.9 | 4.0 |

*Colored hair without pre-color treatment.

As shown by the data in the table above, hair treated with the solution containing zinc gluconate+ calcium chloride as a pre-color treatment unexpectedly retained its color more than the hair treated with the control and each individual material (zinc gluconate alone or calcium chloride alone) after 6 and 10 shampoos. The pre-color treatment with calcium chloride alone resulted in greater color change or color loss as compared to the control or other pre-color treatments. On the hand, while the pre-color treatment with zinc gluconate alone resulted in less color change or color loss as compared to the pre-color treatment with calcium chloride alone, the color change or color loss was still greater than the color change with the pre-color treatment containing zinc gluconate+ calcium chloride.

Example 2

Assessing Color Deposit and Color Protection Against Shampooing (Wash Resistance)

Normal bleached hair swatches (from HIP, about 2 grams) were treated and evaluated as set forth below.

Pre-Color Treatment:

One swatch (Swatch 1) was not treated (control). A second swatch (Swatch 2) was treated with 1.5 grams of the pre-color treatment PT2 in Table 2. Two other hair swatches (Swatch 3 and 4) were treated with the pre-color treatment PT1. The treated hair swatches were then dried.

Color Treatment Only:

The treated hair swatches and an untreated hair swatch (control) were colored using a commercial hair coloring product for 30 mins. The following ratio was used for the coloring process:

1 g hair: 1.5 g of Color Cream: 2.25 g of 20% Vol Peroxide developer.

The hair was rinsed and dried to remove excess dye.

Hair Shampooing:

The colored/treated and untreated hair swatches were washed with an anionic shampoo (containing 12 wt. % sodium laureth sulfate, pH=5.5) and blow dried.

Color Protection and Post-Color Treatment:

For the color protection or wash-resistance study, the colored/treated and untreated hair swatches were washed with an anionic shampoo (containing 12 wt. % sodium laureth sulfate, pH=5.5) 4× and dried. Prior to the 5th wash, 1 g of the inventive Booster formula, B1, was applied to Swatch 4, then left to sit for 20 min. The hair was dried, then shampooed on the 5th wash. A subsequent shampooing for all swatches was made until the 8th shampoo. 1 g of B1 was applied again to Swatch 4, and allowed to sit for 20 min. Following this, the 9th shampoo and 10th shampoo were done for all swatches.

Color Assessment:

For determining the degree of change in the color of hair (e.g. degree of lightening of the color or color deposit), measurements of $L^*$, $a^*$, and $b^*$ values of the hair swatches were obtained before and after 10 shampoos. The $L^*a^*b^*$ colorimetric system is a colorimetric system that assigns each color to a position in a spherical color space. In this color space, the brightness is represented by a position in the ordinate (z-axis) direction, the hue is represented by a position in the circumferential direction, and the chroma is represented by a distance from the center axis. The position on the ordinate (z-axis) representing brightness is designated by $L^*$, and the $L^*$ value changes from 0 corresponding to black to 100 corresponding to white. The positive direction of the x-axis corresponds to a red direction, the positive direction of the y-axis corresponds to a yellow direction, the negative direction of the x-axis corresponds to a green direction, the negative direction of the y-axis corresponds to a blue direction, and the position on the x-axis is designated by $a^*$ of which value changes from −60 to +60 and the position on the y-axis is designated by $b^*$ of which value changes from −60 to +60. The hue and chroma are represented by $a^*$ value and $b^*$ value, respectively. The higher the $L^*$, the lighter the color of the hair; the higher the $a^*$, the more the hue shifts to red (i.e., the hair is redder); and the lower the $b^*$, the more the chroma value shifts to blue. Delta-E (LE) which is calculated from the $L^*$, $a^*$, and $b^*$ values represents the overall color change on the swatches.

Pre-Color Treatments were prepared according to the formulations in Table 2:

TABLE 2

| Ingredient | Pre-Color Treatment 1 (PT1)-Invention Wt. % | Pre-Color Treatment 2 (PT2)-comparative Wt. % |
|---|---|---|
| ZnGluconate | 5 | — |
| CaCl2 | 2.5 | — |
| Hydroxypropyl Starch Phosphate | 5.3 | 5.3 |
| Behentrimonium chloride | 1.6 | 1.6 |
| Stearyl alcohol | 2 | 2 |
| PQ-87 | 2.5 | 2.5 |
| Amodimethicone | 1.5 | 1.5 |
| Caprylyl glycol | 0.6 | 0.6 |
| Water | QS | QS |

Example 2A

In order to assess the efficacy of color deposit provided by the composition of the invention (containing zinc gluconate and calcium chloride), $L^*$ $a^*$ and $b^*$ initial color measurements were taken on the colored hair that was pre-treated with the pre-treatment compositions in Table 2 above. The results are shown in Table 3:

TABLE 3

| Swatch | Pre-Color Treatment | Initial $L^*$ | Initial $a^*$ | Initial $b^*$ | Initial ΔE relative to control |
|---|---|---|---|---|---|
| 1 (control) | — | 25.28 | 17.37 | 11.93 | — |
| 3 | PT1 | 21.82 | 12.86 | 7.22 | 7.38 |

The results above show that unexpectedly, it was found that pre-treating the hair with the inventive formula PT1 before coloring it resulted in significantly greater color deposit as evident from the lower $L^*$ value. There was also a significantly high degree of color change as evident from the delta-E value.

Example 2B

Assessing the efficacy of a pre-color treatment containing Zinc Gluconate and Calcium Chloride followed by a post-color treatment with APTES (aminopropyltriethoxysilane) for hair color protection against shampooing.

The long-lastingness of the artificial color of hair was assessed. Hair was pre-treated with the pre-color treatments as described in Table 2 above before the coloration process. The colored hair was then post-treated with a composition containing APTES (aminopropyltriethoxy silane) as described in Table 4 below. The hair was then shampooed ten times. $L^*$ $a^*$ and $b^*$ initial color measurements were taken after the initial coloration and at the end of the ten shampoos. The efficacy of color protection or resistance of color to fading Booster 1 (B1) (Post-Color)

TABLE 4

| Ingredient | Wt. % |
|---|---|
| aminopropyltriethoxy silane (APTES) | 10 |
| Hydroxyethyl cellulose | 0.7 |
| Oleth-10 | 0.3 |
| Oleth-20 | 0.6 |
| Water | QS |

The colorimetric measurements are provided below in table 5.

TABLE 5

| Swatch | Pre-Color Treatment | Post-Color Booster | $L^*$ | $a^*$ | $b^*$ | ΔE after 10 shampoos |
|---|---|---|---|---|---|---|
| 1 | Control* | — | 35.30 | 15.55 | 16.56 | 11.19 |
| 2 | PT2 | — | 34.26 | 15.87 | 16.08 | 14.57 |
| 3 | PT1 | — | 29.58 | 16.15 | 13.47 | 10.49 |
| 4 | PT1 | B1 | 26.61 | 10.85 | 9.60 | 5.19 |

*Colored hair without pre-color treatment.

Summary:

The results above show that unexpectedly, it was found that the inventive formulas PT1 in combination with B1 protected the color of the colored hair from fading as evident from the lower ΔE values as compared to the values measured from Swatches 1 and 2. The lower ΔE indicates a lower change between the initial color and the color after 10 shampoo cycles (less color loss). The higher ΔE value of the swatch treated with the PT2 formula (comparative) which is very close to the ΔE value of the control swatch indicate that the delivery vehicle (base formula) was not contributing to the color protective effects of the inventive formulas PT1.

In addition, it was unexpectedly found that the pre-color treatment with inventive formulas PT1 in combination with a post-color treatment with B1 provided even greater color protection than PT1 alone as evident from the lower ΔE values which indicate a lower change between the initial color and the color after 10 shampoo cycles (less color loss).

The terms "a," "an," and "the" are understood to encompass the plural as well as the singular.

The expression "at least one" means "one or more" and vice versa, and thus includes individual components as well as mixtures/combinations.

The term "about" when referring to a value, is meant specifically that a measurement can be rounded to the value using a standard convention for rounding numbers. For example, "about 1.5" is 1.45 to 1.54. All values set forth herein can be modified with the term "about," if desired to impart the meaning above, or recited without the term in order to have their ordinary meaning, regardless of whether the term "about" is specifically set forth (or is absent) in conjunction with any particular value in the specification.

When referring to "compositions described herein," all types of compositions are intended unless specifically described otherwise. The "compositions disclosed herein" include the compositions comprising one or more reducing agent, the composition comprising one or more lactones, to oxidizing compositions, etc.

All ranges and values disclosed herein are inclusive and combinable. For examples, any value or point described herein that falls within a range described herein can serve as a minimum or maximum value to derive a sub-range, etc.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A method for artificially coloring hair and inhibiting the coloring from fading, the method comprising:
   (a) treating hair with a pre-color treatment composition comprising about 0.1 wt. % to about 50 wt. % of one or more divalent metal salts of an inorganic acid and about 0.1 wt. % to about 50 wt. % of one or more monovalent or divalent metal salts of an organic acid; and
   (b) treating the hair with a hair coloring composition comprising one or more colorants chosen from oxidative dye precursors, direct dyes, pigments, and mixtures thereof,
   wherein the weight ratio of the one or more divalent metal salts of an inorganic acid to the one or more monovalent or divalent metal salts of an organic acid is from about 10:1 to about 1:10, and
   all weights being based on the total weight of the pre-color treatment composition.

2. The method of claim 1, wherein the one or more divalent metal salts of an inorganic acid are chosen from metal halides, metal hydroxides, metal sulfates, metal oxides, and mixtures thereof.

3. The method of claim 1, wherein the one or more divalent metal salts of an inorganic acid are chosen from salts of calcium, zinc, iron, nickel, copper, silver, magnesium, strontium, barium, manganese, cobalt, and mixtures thereof.

4. The method of claim 1, wherein the one or more divalent metal salts of an organic acid are chosen from salts of calcium, zinc, iron, nickel, copper, silver, magnesium, strontium, barium, manganese, cobalt, and mixtures thereof and wherein the one or more monovalent metal salts of an organic acid are chosen from salts of lithium, sodium, potassium, copper, silver, and mixtures thereof.

5. The method of claim 1, wherein the one or more divalent metal salts of an inorganic acid are chosen from calcium chloride, calcium sulfate, calcium nitrate, calcium carbonate and hydrogen carbonate, calcium phosphate, zinc chloride, zinc sulfate, zinc nitrate, zinc carbonate and hydrogen carbonate, zinc phosphate, magnesium chloride, magnesium sulfate, magnesium nitrate, magnesium carbonate and hydrogen carbonate, magnesium phosphate, strontium chloride, strontium nitrate, barium chloride, barium nitrate, and mixtures thereof.

6. The method of claim 1, wherein the one or more divalent metal salts of an inorganic acid includes a calcium salt.

7. The method of claim 1, wherein the calcium salt is calcium chloride.

8. The method of claim 1, wherein the organic acid of the one or more monovalent or divalent metal salts of an organic acid is chosen from C1 to C9 monocarboxylic or di-carboxylic acids, polycarboxylic acids, hydroxy-carboxylic acids, and fatty acids having at least 10 carbon atoms including ascorbic acid, formic acid, acetic acid, glycolic acid, gluconic acid, lactic acid, mandelic acid, oxalic acid, maleic acid, malonic acid, glyoxylic acid, succinic acid, adipic acid, fumaric acid, sebacic acid, including citric acid, tartaric acid, malic acid, 2-hydroxy malonic acid, 2-hydroxyl n-butyl 1,2,4-tricarboxylic acid, glutaric acid, glucaric acid, 2-hydroxy n-butyl 1,3,4-tricarboxylic acid, pyrrolidone carboxylic acid, phenolsulfonic acid, and salicylic acid.

9. The method of claim 1, wherein the one or more divalent metal salts of an organic acid are chosen from zinc lactate, zinc gluconate, zinc phenolsulfonate, zinc salicylate, zinc pyrrolidone carboxylic acid (Zinc PCA), zinc citrate, zinc ascorbate, their salt derivatives thereof, and mixtures thereof.

10. The method of claim 1, wherein the one or more monovalent metal salts of an organic acid are chosen from sodium ascorbate, sodium formate, sodium gluconate, sodium glutamate, sodium glycolate, sodium glyoxylate, sodium citrate, sodium acetate, sodium lactate, sodium malate, sodium salicylate, potassium acetate, potassium citrate, potassium gluconate, potassium lactate, lithium myristate, lithium stearate, lithium gluconate, silver citrate, silver lactate, silver salicylate, their derivatives thereof, and mixtures thereof.

11. The method of claim 1, wherein the pre-color treatment composition comprises one or more divalent metal salts of an inorganic acid chosen from calcium chloride and one or more divalent metal salts of an organic acid chosen from zinc gluconate.

12. The method of claim 1, wherein the amount of the one or more divalent metal salts of an inorganic acid is greater than the amount of the one or more monovalent or divalent metal salts of an organic acid.

13. The method of claim 1, wherein the amount of the one or more divalent metal salts of an inorganic acid is less than the amount of the one or more monovalent or divalent metal salts of an organic acid.

14. The method of claim 1, wherein the hair coloring composition further comprises one or more oxidizing agents or is capable of being mixed with an oxidizing composition comprising: (i) one or more oxidizing agents; and (ii) a cosmetically acceptable solvent chosen from water and a water/organic solvent mixture; wherein the one or more oxidizing agents are chosen from peroxides, persulfates, perborates, percarbonates, alkali metal bromates, ferricyanides, laccases, peroxidases, redox enzymes, their salts thereof, and mixtures thereof.

15. The method of claim 1, wherein upon treating the hair with the pre-color treatment composition in (a), the pre-color treatment composition is allowed to remain on the hair for at least 30 seconds before treating the hair with the hair coloring composition in (b).

16. The method of claim 1, further comprising a step of treating the hair with a post-color treatment composition after treating the hair with the hair coloring composition in (b).

17. The method of claim 16, wherein the post-color treatment composition comprises from about 1 wt. % to about 30 wt. %, based on the total weight of the composition, of one or more silane compounds corresponding to formula (Ia):

$$R_1Si(OR_2)_z(R_3)_x(OH)_y \quad (Ia)$$

in which:
R$_1$ is a cyclic or acyclic, linear or branched, saturated or unsaturated C$_1$-C$_{22}$ hydrocarbon-based chain, which may be substituted with a group chosen from amine groups NH$_2$ or NHR (R being a linear or branched C$_1$-C$_{20}$ alkyl, a C$_3$-C$_{40}$ cycloalkyl or a C$_6$-C$_{30}$ aromatic radical); a hydroxyl group (OH), a thiol group, an aryl group, which may be substituted with an NH$_2$ or NHR group; it being possible for R1 to be interrupted with a heteroatom (O, S or NH) or a carbonyl group (CO),
R$_2$ and R$_3$, which may be identical or different, represent a linear or branched alkyl group comprising from 1 to 6 carbon atoms,
y denotes an integer ranging from 0 to 3, and
z denotes an integer ranging from 0 to 3, and
x denotes an integer ranging from 0 to 2, with z+x+y=3.

18. The method of claim 17, wherein the one or more silane compounds are chosen from 3-aminopropyltriethoxysilane (APTES), 3-aminoethyltriethoxysilane (AETES), 3-aminopropylmethyldiethoxysilane, N-(2-aminoethyl)-3-aminopropyltriethoxysilane, 3-(m-aminophenoxy)propyltrimethoxysilane, p-aminophenyltrimethoxysilane and N-(2-aminoethylaminomethyl) phenethyltrimethoxysilane, their oligomers, and mixtures thereof.

19. The method of claim 17, wherein the post-color treatment composition is applied to the colored hair within a period of time of up to about 24 hours of the hair being colored and is allowed to remain on the hair for at least 1 minute.

20. A kit for artificially coloring hair, the kit comprising:
(i) a pre-color treatment component comprising one or more divalent metal salts of an inorganic acid and one or more monovalent or divalent metal salts of an organic acid;
(ii) a hair coloring composition comprising one or more colorants chosen from oxidative dye precursors, direct dyes, pigments, and mixtures thereof
(iii) an oxidizing composition comprising: (i) one or more oxidizing agents; and (ii) a cosmetically acceptable solvent chosen from water and a water/organic solvent mixture; wherein the one or more oxidizing agents are chosen from peroxides, persulfates, perborates, percarbonates, alkali metal bromates, ferricyanides, laccases, peroxidases, redox enzymes, their salts thereof, and mixtures thereof; and
(iv) optionally, a post-color treatment composition comprising from about 1 wt. % to about 30 wt. %, based on the total weight of the post-color treatment composition, of one or more silane compounds corresponding to formula (Ia):

$$R_1Si(OR_2)_z(R_3)_x(OH)_y \quad (Ia)$$

in which:
R$_1$ is a cyclic or acyclic, linear or branched, saturated or unsaturated C$_1$-C$_{22}$ hydrocarbon-based chain, which may be substituted with a group chosen from amine groups NH$_2$ or NHR (R being a linear or branched C$_1$-C$_{20}$ alkyl, a C$_3$-C$_{40}$ cycloalkyl or a C$_6$-C$_{30}$ aromatic radical); the hydroxyl group (OH), a thiol group, an aryl group, which may be substituted with an NH$_2$ or NHR group; it being possible for R1 to be interrupted with a heteroatom (O, S or NH) or a carbonyl group (CO),
R$_2$ and R$_3$, which may be identical or different, represent a linear or branched alkyl group comprising from 1 to 6 carbon atoms,
y denotes an integer ranging from 0 to 3, and
z denotes an integer ranging from 0 to 3, and
x denotes an integer ranging from 0 to 2, with z+x+y=3;
wherein the one or more divalent metal salts of an inorganic acid and the one or more monovalent or divalent metal salts of an organic acid are applied to the hair separately or together as a pre-color treatment composition such that the total amount of the metal salts applied onto the hair is at least 0.2 wt. %.

21. A method for artificially coloring hair and inhibiting the color from fading, the method comprising:
treating the hair with a pre-color treatment composition comprising about 0.1 wt. % to about 50 wt. % of one or more divalent metal salts of an inorganic acid, based on the total weight of the pre-color treatment composition; and about 0.1 wt. % to about 50 wt. % of one or more monovalent or divalent metal salts of an organic acid, based on the total weight of the pre-color treatment composition;
treating the hair with a hair coloring composition comprising one or more colorants chosen from oxidative dye precursors, direct dyes, pigments, and mixtures thereof; and
treating the hair with about 1 wt. % to about 30 wt. % of one or more silane compounds corresponding to formula (Ia):

$$R_1Si(OR_2)_z(R_3)_x(OH)_y \quad (Ia)$$

in which:
R$_1$ is a cyclic or acyclic, linear or branched, saturated or unsaturated C$_1$-C$_{22}$ hydrocarbon-based chain, which may be substituted with a group chosen from amine groups NH$_2$ or NHR (R being a linear or branched C$_1$-C$_{20}$ alkyl, a C$_3$-C$_{40}$ cycloalkyl or a C$_6$-C$_{30}$ aromatic radical); the hydroxyl group (OH), a thiol group, an aryl group, which may be substituted with an NH$_2$ or NHR group; it being possible for R1 to be interrupted with a heteroatom (O, S or NH) or a carbonyl group (CO),
R$_2$ and R$_3$, which may be identical or different, represent a linear or branched alkyl group comprising from 1 to 6 carbon atoms,
y denotes an integer ranging from 0 to 3, and
z denotes an integer ranging from 0 to 3, and
x denotes an integer ranging from 0 to 2, with z+x+y=3; and
wherein when the one or more silane compounds of formula (Ia) are employed to treat hair, they are applied to the hair as a post-color treatment in order to boost the anti-fading properties of the artificial color of hair.

22. The method of claim 21, wherein the one or more divalent metal salts of an inorganic acid are chosen from metal halides, metal hydroxides, metal sulfates, metal oxides, and mixtures thereof and from salts of calcium, zinc, iron, nickel, copper, silver, magnesium, strontium, barium, manganese, cobalt, and mixtures thereof.

23. The method of claim 21, wherein the one or more divalent metal salts of an organic acid are chosen from salts of calcium, zinc, iron, nickel, copper, silver, magnesium, strontium, barium, manganese, cobalt, and mixtures thereof and wherein the one or more monovalent metal salts of an organic acid are chosen from salts of lithium, sodium, potassium, copper, silver, and mixtures thereof.

24. The method of claim 21, wherein the one or more divalent metal salts of an inorganic acid are chosen from calcium chloride, calcium sulfate, calcium nitrate, calcium carbonate and hydrogen carbonate, calcium phosphate, zinc chloride, zinc sulfate, zinc nitrate, zinc carbonate and hydrogen carbonate, zinc phosphate, magnesium chloride, magnesium sulfate, magnesium nitrate, magnesium carbonate and hydrogen carbonate, magnesium phosphate, strontium chloride, strontium nitrate, barium chloride, barium nitrate, and mixtures thereof.

25. The method of claim 21, wherein the organic acid of the one or more monovalent or divalent metal salts of an organic acid is chosen from C1 to C9 monocarboxylic or di-carboxylic acids, polycarboxylic acids, hydroxy-carboxylic acids, and fatty acids having at least 10 carbon atoms including ascorbic acid, formic acid, acetic acid, glycolic acid, gluconic acid, lactic acid, mandelic acid, oxalic acid, maleic acid, malonic acid, glyoxylic acid, succinic acid, adipic acid, fumaric acid, sebacic acid, including citric acid, tartaric acid, malic acid, 2-hydroxy malonic acid, 2-hydroxyl n-butyl 1,2,4-tricarboxylic acid, glutaric acid, glucaric acid, 2-hydroxy n-butyl 1,3,4-tricarboxylic acid, pyrrolidone carboxylic acid, phenolsulfonic acid, and salicylic acid.

26. The method of claim 21, wherein the one or more monovalent or divalent metal salts of an organic acid are chosen from zinc lactate, zinc gluconate, zinc phenolsulfonate, zinc salicylate, zinc pyrrolidone carboxylic acid (Zinc PCA), zinc citrate, zinc ascorbate, sodium ascorbate, sodium formate, sodium gluconate, sodium glutamate, sodium glycolate, sodium glyoxylate, sodium citrate, sodium acetate, sodium lactate, sodium malate, sodium salicylate, potassium acetate, potassium citrate, potassium gluconate, potassium lactate, lithium myristate, lithium stearate, lithium gluconate, silver citrate, silver lactate, silver salicylate, their derivatives thereof, and mixtures thereof.

27. The method of claim 21, wherein the pre-color treatment composition comprises one or more divalent metal salts of an inorganic acid chosen from calcium chloride and one or more divalent metal salts of an organic acid chosen from zinc gluconate.

28. The method of claim 21, wherein the amount of the one or more divalent metal salts of an inorganic acid is greater than the amount of the one or more monovalent or divalent metal salts of an organic acid.

29. The method of claim 21, wherein the amount of the one or more divalent metal salts of an inorganic acid is less than the amount of the one or more monovalent or divalent metal salts of an organic acid.

30. The method of claim 21, wherein the hair coloring composition further comprises one or more oxidizing agents or is capable of being mixed with an oxidizing composition comprising: (i) one or more oxidizing agents; and (ii) a cosmetically acceptable solvent chosen from water and a water/organic solvent mixture; wherein the one or more oxidizing agents are chosen from peroxides, persulfates, perborates, percarbonates, alkali metal bromates, ferricyanides, laccases, peroxidases, redox enzymes, their salts thereof, and mixtures thereof.

31. The method of claim 21, wherein the pre-color treatment is allowed to remain on the hair for about 1 minute to about 1 hour at a temperature of about 20° C. to about 45° C. before treating the hair with the coloring composition.

32. The method of claim 21, wherein when the post-color treatment is employed, it is applied to the colored hair within a period of time ranging from about one hour up to about 24 hours of the hair being colored and is allowed to remain on the hair for about 1 minute to about 1 hour at a temperature of about 20° C. to about 45° C.

33. A pre-color treatment composition comprising:
about 0.1 wt. % to about 50 wt. % of one or more divalent metal salts of an inorganic acid chosen from calcium chloride, calcium sulfate, calcium nitrate, calcium carbonate and hydrogen carbonate, calcium phosphate, zinc chloride, zinc sulfate, zinc nitrate, zinc carbonate and hydrogen carbonate, zinc phosphate, magnesium chloride, magnesium sulfate, magnesium nitrate, magnesium carbonate and hydrogen carbonate, magnesium phosphate, strontium chloride, strontium nitrate, barium chloride, barium nitrate, and mixtures thereof; and
about 0.1 wt. % to about 50 wt. % of one or more monovalent or divalent metal salts of an organic acid chosen from zinc lactate, zinc gluconate, zinc phenolsulfonate, zinc salicylate, zinc pyrrolidone carboxylic acid (Zinc PCA), zinc citrate, zinc ascorbate, sodium ascorbate, sodium formate, sodium gluconate, sodium glutamate, sodium glycolate, sodium glyoxylate, sodium citrate, sodium acetate, sodium lactate, sodium malate, sodium salicylate, potassium acetate, potassium citrate, potassium gluconate, potassium lactate, lithium myristate, lithium stearate, lithium gluconate, silver citrate, silver lactate, silver salicylate, their derivatives thereof, and mixtures thereof;
wherein the pre-color treatment composition is applied onto hair before artificially coloring the hair;
all weights based on the total weight of the composition.

34. The pre-color treatment composition of claim 33, further comprising one or more of a thickening agent, a cationic agent, a surfactant, a silicone, and a cosmetically acceptable solvent.

35. The pre-color treatment composition of claim 33, wherein the weight ratio of the one or more divalent metal salts of an inorganic acid to the one or more monovalent or divalent metal salts of an organic acid is from about 10:1 to about 1:10.

36. A post-color treatment composition comprising about 1 wt. % to about 20 wt. %, based on the total weight of the composition, of one or more silane compounds corresponding to formula (Ia):

in which:
R$_1$ is a cyclic or acyclic, linear or branched, saturated or unsaturated C$_1$-C$_{22}$ hydrocarbon-based chain, which may be substituted with a group chosen from amine groups NH$_2$ or NHR (R being a linear or branched C$_1$-C$_{20}$ alkyl, a C$_3$-C$_{40}$ cycloalkyl or a C$_6$-C$_{30}$ aromatic radical); the hydroxyl group (OH), a thiol group, an aryl group, which may be substituted with an NH$_2$ or NHR group; it being possible for R1 to be interrupted with a heteroatom (O, S or NH) or a carbonyl group (CO), $R_2$ and $R_3$, which may be identical or different, represent a linear or branched alkyl group comprising from 1 to 6 carbon atoms, y denotes an integer ranging from 0 to 3, and z denotes an integer ranging from 0 to 3, and x denotes an integer ranging from 0 to 2, with $z+x+y=3$;

wherein the post-color treatment composition is for the treatment of artificially colored hair.

37. The post-color treatment composition of claim 36, further comprising one or more of a thickening agent, a cationic agent, a nonionic surfactant, a silicone, and a cosmetically acceptable solvent.

* * * * *